(12) United States Patent
Tomcany et al.

(10) Patent No.: US 7,426,761 B2
(45) Date of Patent: *Sep. 23, 2008

(54) PATIENT IMMOBILIZATION DEVICE

(76) Inventors: Brian Tomcany, 19431 Blue Spruce Dr., Strongsville, OH (US) 44149; John A. Helmsderfer, 6909 Kenwood Rd., Cincinnati, OH (US) 45243

( * ) Notice: Subject to any disclaimer, the term of this patent is extended or adjusted under 35 U.S.C. 154(b) by 132 days.

This patent is subject to a terminal disclaimer.

(21) Appl. No.: 11/101,749

(22) Filed: Apr. 8, 2005

(65) Prior Publication Data

US 2005/0241068 A1    Nov. 3, 2005

Related U.S. Application Data

(63) Continuation-in-part of application No. 10/335,523, filed on Dec. 31, 2002, now Pat. No. 7,036,167.

(60) Provisional application No. 60/359,622, filed on Feb. 26, 2002.

(51) Int. Cl.
*A61G 1/04* (2006.01)
*A61G 1/044* (2006.01)
*A61G 1/00* (2006.01)

(52) U.S. Cl. ................................ 5/628; 5/622

(58) Field of Classification Search ............ 5/628, 5/622, 637, 640, 636, 643, 625, 626, 627; 128/870, 869, 846, 845
See application file for complete search history.

(56) References Cited

U.S. PATENT DOCUMENTS

| | | | |
|---|---|---|---|
| 2,377,940 A | 6/1945 | Hughes | |
| 2,391,928 A | 1/1946 | Seib | 5/82 |
| 2,394,264 A | 2/1946 | Robinson | 5/82 |
| 2,511,061 A | 6/1950 | Hughes | |
| 2,675,564 A | 4/1954 | Hughes | |
| 2,770,465 A | 11/1956 | Dandurand | 280/12 |
| 3,222,080 A | 12/1965 | Kinraide | 280/18 |
| 3,449,776 A | 6/1969 | Brock | 5/627 |
| 3,650,523 A | 3/1972 | Darby, Jr. | 5/603 |
| 3,653,079 A | 4/1972 | Bourgraf et al. | 5/82 |
| 3,689,945 A | 9/1972 | Laerdal | 5/82 |

(Continued)

OTHER PUBLICATIONS

Alliance Medical Catalog, *Laerdal® Speedblocks® Head Immobilizer*, http://www.allmed.net/catalog/showitem.php/3431, Sep. 29, 2002, pp. 1.

(Continued)

*Primary Examiner*—Alexander Grosz
(74) *Attorney, Agent, or Firm*—Wood, Herron & Evans LLP

(57) ABSTRACT

A patient immobilization device comprises a backboard having a front side and a back side, and a pair of opposing paddles slidably mounted on the backboard. The paddles are configured to move between a storage position and a support position, to support the head of a patient. Each paddle has a leg portion depending there from and extends through a respective slot formed in the backboard between the front and back and sides. A spanning portion of the paddle depends from the leg portion and engages the back side of the backboard to secure the paddle to the backboard. The spanning portion moves in a generally arcuate path between the storage and support positions.

15 Claims, 17 Drawing Sheets

U.S. PATENT DOCUMENTS

| | | | |
|---|---|---|---|
| 3,707,734 A | 1/1973 | Matthews | 5/82 |
| 3,737,923 A | 6/1973 | Prolo | 5/82 |
| 3,775,782 A | 12/1973 | Rice et al. | 5/82 |
| 3,890,659 A | 6/1975 | Stuabs | 5/82 |
| 4,024,861 A | 5/1977 | Vincent | 128/87 |
| 4,033,000 A | 7/1977 | Bonifay | 5/82 |
| 4,064,574 A | 12/1977 | Schnitzler | 5/82 |
| 4,124,908 A | 11/1978 | Burns et al. | 5/82 |
| 4,252,113 A | 2/1981 | Scire | 5/628 |
| 4,267,830 A | 5/1981 | Vick | 128/87 |
| 4,347,635 A | 9/1982 | Eisenhauer | 441/40 |
| 4,369,982 A | 1/1983 | Hein et al. | 280/47.13 |
| 4,480,345 A | 11/1984 | Dunn | 5/82 |
| 4,571,757 A | 2/1986 | Zolecki | 5/628 |
| 4,771,493 A | 9/1988 | Park | |
| 4,794,656 A | 1/1989 | Henley, Jr. | 5/82 |
| 4,928,711 A | 5/1990 | Williams | 128/869 |
| 5,201,089 A | 4/1993 | Ferreira | 5/627 |
| 5,211,185 A | 5/1993 | Garth et al. | 128/870 |
| 5,265,625 A | 11/1993 | Bodman | 128/869 |
| 5,395,158 A | 3/1995 | Cordia | 297/393 |
| 5,414,883 A | 5/1995 | Fangrow, Jr. | 5/625 |
| D367,834 S | 3/1996 | Beavers et al. | D12/133 |
| 5,657,766 A | 8/1997 | Durham | 128/870 |
| 5,729,850 A | 3/1998 | Eskeli | 5/621 |
| D403,423 S | 12/1998 | Bologovsky et al. | D24/190 |
| 5,944,016 A | 8/1999 | Ferko, III | 128/869 |
| 5,950,627 A | 9/1999 | Bologovsky et al. | 128/869 |
| D425,992 S | 5/2000 | Davis et al. | D24/189 |
| 6,170,486 B1 | 1/2001 | Islava | 128/869 |
| 6,244,270 B1 | 6/2001 | Lutian et al. | 128/869 |
| 6,327,723 B1 | 12/2001 | Knight | 5/628 |
| D462,448 S | 9/2002 | Huttner | D24/191 |
| 6,443,157 B1 | 9/2002 | Sargent | 128/870 |
| D469,541 S | 1/2003 | Cheatham | D24/191 |
| 6,637,057 B2 | 10/2003 | Phillips et al. | |
| 6,659,104 B2 | 12/2003 | Kiefer et al. | 128/870 |
| 6,862,759 B2 | 3/2005 | Hand et al. | 5/430 |
| 2004/0016057 A1 | 1/2004 | Traut et al. | |
| 2004/0049852 A1 | 3/2004 | Phillips et al. | |

OTHER PUBLICATIONS

Alliance Medical Catalog, *STI Sta-BLok™ Head Immobilizer*, http://www.allmed.net/catalog/showitem.php/3446, Sep. 29, 2002, p. 1.
Alliance Medical Catalog, *Morrison Medical Head Blocks™, Disposable Foam*, http://www.allmed.net/catalog/showitem.php/4398, Sep. 29, 2002, p. 1.
Alliance Medical Catalog, *Laerdal® BaXstrap® Spineboard*, http://www.allmed.net/catalog/showitem.php/3454, Sep. 29, 2002, p. 1.
Alliance Medical Catalog, *Dispos-A-Board® Backboard*, http://www.allmed.net/catalog/showitem.php/3463, Sep. 29, 2002, pp. 1-2.
Alliance Medcal Catalog, *Bashaw Rough Terrain CID*, http://www.allmed.net/catalog/showitem.php/3434, Sep. 29, 2002, p. 1.
Alliance Medical Catalog, *Allied LSP SpineX® Backboard*, http://www.allmed.net/catalog/showitem.php/3449, Sep. 29, 2002, p. 1.
Alliance Medical Catalog, *Allied LSP Stabilizer® Backboard*, http://www.allmed.net/catalog/showitem.php/3450, Sep. 29, 2002, p. 1.
Alliance Medical Catalog, *I-Tec® Multi-Grip Head Immobilizer*, http://www.allmed.net/catlog/showitem.php/3438, Sep. 29, 2002, p. 1.
Alliance Medical Catalog, *EP&R Bak-Pak*, http://www.allmed.net/catalog/showitem.php/4115, Sep. 29, 2002, p. 1.
Alliance Medical Catalog, *Morrison Medical Sticky Blocks™ Head Immobilizers*, http://www.allmed.net/catalog/showitem.php/4396, Sep. 29, 2002, p. 1.
Alliance Medical Catalog, *Morrison Medical Head Vise™ I Reusable Head Immobilizer*, http://www.allmed.net/catalog/showitem.php/3444, Sep. 29, 2002, p. 1.
Alliance Medical Catalog, *Bashaw Infant CID*, http://www.allmed.net/catalog/showitem.php/4124, Sep. 29, 2002, pp. 1-2.
Alliance Medical Catalog, *Morrison Medical Head Blocks?™ Set, With Straps*, http://www.allmed.net/catalog/showitem.php/4401, Sep. 29, 2002, pp. 1-2.
Alliance Medical Catalog, *Morrison Medical Head Vise™ III*, http://www.allmed.net/catalog/showitem.php/4410, Sep. 29, 2002, p. 1.
Alliance Medical Catalog, Laerdal® HeadBed® II Head Immobilization Device, http://www.allmed.net/catalog/showitem.php/3432, Sep. 29, 2002, p. 1.
Alliance Medical Catalog, *Morrison Medical New & Improved Head Vise™ II Head Immobilizer*, http://www.allmed.net/catalog/showitem.php/3445, Sep. 29, 2002, p. 1.
Pro-Lite XT, *Pro-Lite XT®*, http://www.allmed.net/catalog/showitem.php/3447, Sep. 29, 2002, pp. 1-2.
Pro-Lite Spineboard, *Pro-Lite Spineboard®*, http://www.allmed.net/catalog/showitem.php/3448, Sep. 29, 2002, p. 1.
Dispos-O-Bag, *Dispos-O-Bag® Head-On® Block*, http://www.allmed.net/catalog/showitem/php/3441, Sep. 29, 2002, p. 1.
Ferno, *Model 455 HeadHugger™ Disposable Head Immobilizer*, http://emergency.ferno.com/immobilize/model455.htm, Sep. 29, 2002, p. 1.
Ferno, *740/750 Series Phenolic Wooden Backboards*, http://emergency.ferno.com/immobilie/model_740_750.htm, Sep. 29, 2002, p. 1.
Iron Duck Catalog, *Ultra Loc Backboard & Head Loc II*, http://www.ironduck.com/catalog.epl?ProductID=118, Sep. 29, 2002, pp. 1-4.
Junkin Safety Appliance Company, *Junkin Safety Backboards*, http://www.junkinsafety.com/products/backbrd.html, Sep. 29, 2002, pp. 1-2.
Ferno, *Millenia™ Plastic Backboards*, http://emergency.ferno.com/immobilize/bckbrds.htm, Sep. 29, 2002, p. 1.
Morrison Medical, *Morrison Medical—Head Immobilzers*, http://www.mossisonmed.com/head.htm, Sep. 29, 2002, pp. 1-2.
NAJO™ Backboards, *NAJO™ Backboards*, http://reefmedical.com./au/najo, Sep. 29, 2002, pp. 1-3.
PMX, *PMX Backboard*, http://www.pmxmedical.com/catalog/page30.html, Sep. 29, 2002, p. 1.

PATIENT IMMOBILIZATION DEVICE

RELATED APPLICATIONS

This application is a Continuation-In-Part application of U.S. patent application Ser. No. 10/335,523, filed Dec. 31, 2002, and entitled "Patient Immobilization Device," and now issued as U.S. Pat. No. 7,036,167, which application claims priority to U.S. Provisional Application Ser. No. 60/359,622, filed Feb. 26, 2002, and entitled "Backboard with Head Immobilizer," which applications are incorporated herein by reference in their entireties.

FIELD OF THE INVENTION

This invention relates generally to a patient immobilization device including a backboard and head immobilizer used to support and immobilize injured patients.

BACKGROUND OF THE INVENTION

In accidents involving apparent injury to the head, neck, and/or spine, the patient is immobilized for treatment and transport. Specifically, the head and cervical spine areas of the patient are routinely immobilized to prevent further injury during transport to a medical facility. For such immobilization, devices such as rigid backboards are typically used to support and assist in immobilizing the patient during this time. A head immobilization device or immobilizer is used with the backboard. For example, the patient is placed on a board and stiff pillows or blocks are placed tightly on either side of his head. A combination of headstraps, chinstraps, and tapes are then tightly secured over the pillows/blocks and the board to fixedly hold the patient's head in place on the board.

Currently, there are several typical types of head immobilizers in use that are incorporated generally with a flat backboard. One type of head immobilization system utilizes a pair of reusable blocks, which are formed of a pliant, yet supportive material such as rigid foam or a suitable vinyl material. Generally, such blocks are secured to a board with hook and loop fastening structures, such as Velcro®.

Another type of immobilizer is disposable and utilizes inexpensive cardboard, which is manipulated to form a support structure for the head and neck. Generally, such a cardboard material is temporarily coupled to a backboard with an adhesive material. Other types of head immobilization systems utilize a combination of reusable and disposable elements that may be temporarily coupled to a backboard.

Although such systems have proven suitable for use with a backboard to immobilize a patient, they present other problems. While reusable foam or vinyl blocks may be relatively inexpensive, due to reuse, they must be repeatedly cleaned and maintained after each use to prevent the transmission of unsafe pathogens, either through blood or other bodily fluid, such as vomit. Repeated cleaning of the blocks may cause premature deterioration of the blocks and their covering or outer skin. Also, foam material can effectively turn into a sponge, thus trapping blood-borne pathogens and other pathogens. As such, after a certain amount of use, even reusable blocks will need to be replaced.

Another problem with such reusable blocks is that they are difficult to store when not in use. Emergency medical vehicles provide little excess storage space for equipment and materials. Therefore, generally, the reusable blocks are stored in a location that is remote from the tall narrow opening provided for backboard storage, such as in an ambulance. Separation of key pieces of the patient immobilization equipment for the purpose of storage can often lead to lost or misplaced items. This is particularly critical at an accident or medical emergency when the retrieval time may be critical for the patient's health and well being. Accident scenes are often chaotic environments involving multiple emergency medical service providers. Therefore, any lost time involved in gathering up all the pieces necessary for head and neck support and patient immobilization is particularly undesirable.

Furthermore, because the blocks are separate pieces from the board, they often become lost or are mistakenly collected by other medical providers, such as at an accident scene or during equipment recollection at a medical facility. As may be appreciated, patients may come into a hospital emergency room, supported and immobilized on the equipment of several rescue teams. The rescue teams then return to the scene of the accident for other patients or victims, or go out on other calls, and they leave the equipment at the hospital with their patients. After the equipment is removed, it is often placed in a common area for the various teams to recover. During such recovery, one team or unit may inadvertently grab the equipment of another unit.

Single-use, disposable head immobilization devices and systems do have some advantages over reusable systems in that they are generally smaller, are easier to store in an ambulance, and do not have to be recovered because they are discarded after one use. Furthermore, since they are not reused, they do not have to be cleaned and they do not present a significant risk with respect to transmission of unsafe bodily fluids from one patient to the next. However, because they are single-use devices, an emergency medical service provider must purchase and store a sufficient amount so as not to run out during response to an emergency situation. This requires frequent purchases, control of inventory at a central storage area, and distribution of the devices to all the vehicles that would use the devices. This essentially increases the overall cost of the equipment for an emergency service provider.

Furthermore, because such single-use devices often utilize adhesives for attachment to a backboard, repeated attachments require the removal and cleaning of the board proximate the adhesive. Repeated cleaning of the adhesive portions of the device after each use becomes a nuisance for the user.

Another drawback with disposal head immobilization devices is that they often use cardboard as their primary construction material. Many patients and the public, in general, do not perceive cardboard as a particularly robust material as compared with other materials used to make emergency medical equipment, such as rigid plastic used to make backboards and cervical collars. Patient and public perception of high quality care and equipment materials is an important factor in providing satisfactory service from emergency medical providers. Notwithstanding perception, the robustness of the devices themselves is important. Some patients may require intubation tubes to assist with breathing. Intubated patients who dislodge their tubes would have to be immediately attended to in order to maintain an unobstructed airway. One prevalent cause of a dislodged intubation tube is movement, particularly head movement, which can occur when a patient is panicking or is having a seizure. Therefore, it is important to have robust head immobilization devices that are sufficiently coupled with the backboard in order to keep patients from dislodging their intubation tubes.

U.S. patent application Ser. No. 10/335,523 filed Dec. 31, 2002 and entitled "Patient Immobilization Device," addresses various of the drawbacks of the prior art and provides advantages to assist in patient care. The present application and inventions disclosed therein improve on the art and address various of the above drawbacks in the prior art and provides other advantages to assist in the care of patients requiring head and neck immobilization.

SUMMARY OF THE INVENTION

The patient immobilization device of the present invention comprises a backboard having a front side and a back side. Generally, the patient is placed on the front side (or top side) while the back side (or bottom side) rests against a surface, such as the ground. A pair of opposing paddles are slidably mounted on the backboard and are configured to move between a storage position against the backboard and a support position where they support the head and neck of a patient lying on the backboard. The paddles are stored flat with the backboard and are folded up when used. Each paddle has a leg portion depending there from and extending through a respective slot formed in the backboard between the front and back sides to couple the paddles with the backboard.

In one aspect, each paddle includes a first friction surface, which is positioned proximate the front side of the backboard. A cooperating second friction surface of the paddle is positioned proximate the back side of the backboard. When the paddle is in the storage position or between the storage and support positions, the friction surfaces generally do not engage the backboard. As such, when the paddle is moved between the storage position and the support position, it can be readily moved laterally on the backboard to determine a proper lateral position for each paddle and the proper spacing between the paddles for supporting the head/neck of a patient on the backboard. When the paddle is moved into the support position, the first and section friction surfaces engage the backboard, particularly with respect to the front side and back side of the backboard. The first and second friction surfaces cooperate to fix the lateral position of each paddle and the respective spacing there between.

In one embodiment of the invention, the paddle comprises a leg portion depending from the paddle extending through a respective slot, formed in the backboard between the front and back sides. The paddle might use a single leg portion or multiple leg portions. The leg portion positions the second friction surface proximate the back side of the backboard. In one embodiment, a pin structure is coupled with the paddle and, in particular, with the leg portion. The pin structure defines the second friction surface. In one embodiment, the pin structure has a T-shaped cross-section with a portion of the T-shaped cross-section forming the second friction surface. The first friction surface on the paddle may be defined by a rib, which is positioned proximate the front side of the backboard. To allow for proper movement and adjustment of the paddles when they are between the storage position and support position, the second friction surface is positioned laterally outwardly from the first friction surface with respect to the center longitudinal axis of the backboard. In the storage position a recess is formed for receiving the paddles. The paddles include side ribs for engaging the slot sides to lock the paddles in the storage position.

In another aspect of the present invention, when the paddles are in a support position and are held against the head of a patient, such as with straps, the opposing friction surfaces cooperate to fix the lateral position of the paddles. Prior to securing the paddles around the patient's head, they snap into place when folded to the support position. The paddles slide along slots formed along the backboard and a snap structure on the paddle engages the slot when the paddle is folded to lock the paddle in the support position, thereby preventing it from falling over when positioned with respect to the patient's head.

In another aspect of the present invention, the paddles include a head-engaging portion that forms a cup structure. A pliable pad, generally in the shape of a head-engaging portion, is removably mounted in the cup structure of the paddle for the patient's comfort when the paddles are positioned on either side of the patient's head. Preferably, the dimensions of the pliable form are larger than those of the cup structure that is frictionally mounted therein.

In another aspect of the invention, a cushion is removably mounted in the recess in the backboard front side, between the paddles. The cushion provides comfort to the patient's head and has a contoured bottom surface. The recess containing the cushion includes drain holes formed in the floor of the recess and the contour of the cushion extends partially above the recessed floor to expose the drain holes to allow fluid to drain out of the recess.

In yet another aspect of the invention, a securement strap is configured to span between paddles in a support position for securing a patient's head. The securement straps include a secured end that is secured in a rotatable fashion to a respective paddle. A rotatable buckle on the opposing paddle is utilized for securing the free end of the strap.

In another aspect of the invention, the paddles are removable from the backboard for cleaning and/or replacement. To that end, in one embodiment, a portion of the paddle extending through the slot in the backboard, includes an aperture for receiving a pin structure. The pin structure is slidable in the aperture for securing the paddle in place on the backboard. The pin structure includes a snap structure, which engages the aperture to lock the pin structure and secure the paddle. The snap structure is releasable for removing the pin structure, thereby allowing the paddle to be removed from the backboard. In another embodiment, a cross-slot is positioned at one end of the paddle slot to allow the paddle to be removed.

In another aspect of the invention, the paddle includes the head-engaging portion, which has an accessory mount positioned thereon. The accessory mount is configured for capturing an accessory used by the patient on the backboard to hold the accessory proximate the patient's head. In one embodiment, the accessory mount includes one or more slots. The accessory mount may also include one or more clip structures. The slots and/or clip structures are configured for holding tubes, such as oxygen tubes, used by the patient. Alternatively, the accessory mount might be used to capture straps or mounting structures used for various accessories, such as an oxygen mask.

To ensure proper position of the patient on the backboard, ruler indicia extend along the length of the backboard and includes a section positioned proximate the paddles for use in positioning the patient's body and head with respect to the paddles with respect to immobilization.

These features and other features of the present invention are discussed herein below with respect to the Detailed Description.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

FIG. 1 is a perspective view of one embodiment of the present invention.

FIG. 1D is a perspective side view of an embodiment of a paddle of the invention.

FIG. 20 is an end cross-sectional view of another embodiment of the present invention.

DETAILED DESCRIPTION OF SPECIFIC EMBODIMENTS OF THE INVENTION

Figure 1A:
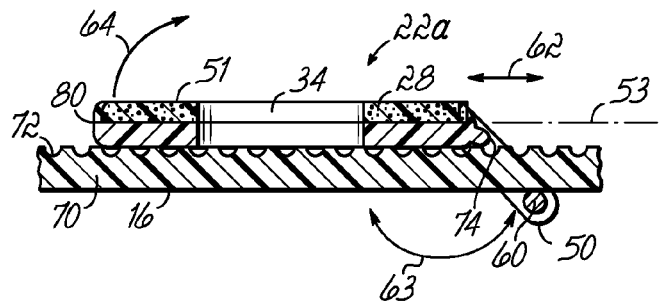
FIG. 1A is a side view, in cross-section, of a paddle of the present invention, in a storage position.

Referring to FIG. 1, a perspective view of a patient immobilization device 10 of the invention is illustrated. Generally, such a device comprises a backboard or backboard portion 12, having a top side or front side 14, and a bottom side or back side 16. In use, a patient would generally be placed on the front side 14, with their feet at the foot end 18 of the backboard and their head at the head end 20 of the backboard. For securing the head and neck of a patient, the invention utilizes a pair of opposing paddles 22a and 22b, which are slidably mounted on the backboard 12, and are configured, in a support position, to support the head and neck of a patient. Embodiments of the paddles 22a, 22b are illustrated in the support position in FIG. 1.

Figure 1B:
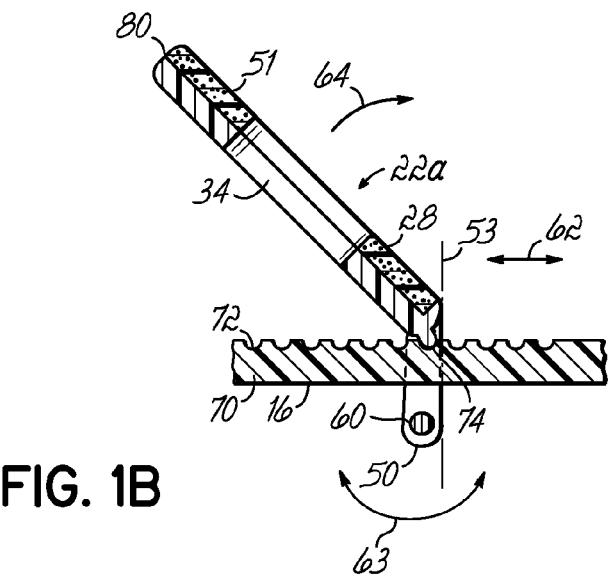
FIG. 1B is a side view, similar to FIG. 1A, of a paddle moving between a storage position and a support position.
Figure 1C:
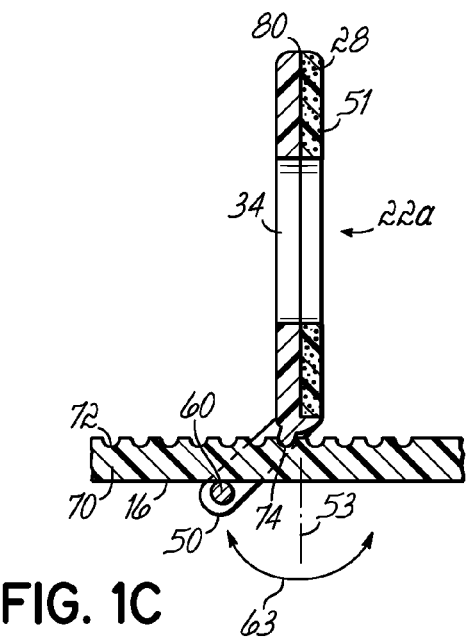
FIG. 1C is a side view, in cross-section similar to FIG. 1A, of a paddle in the support position.
Figure 2O:
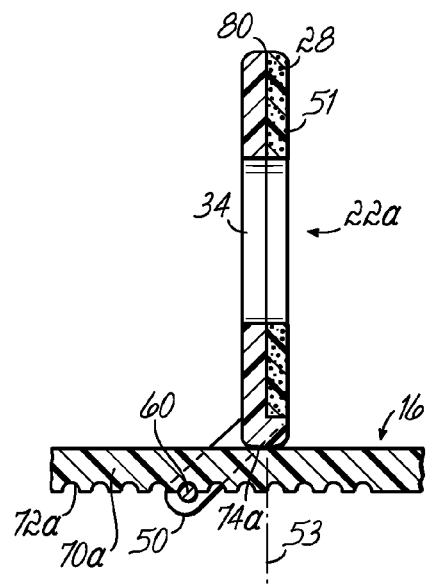
FIG. 2 is a partial perspective view of one embodiment of the invention illustrating an immobilized patient.
Figure 2:
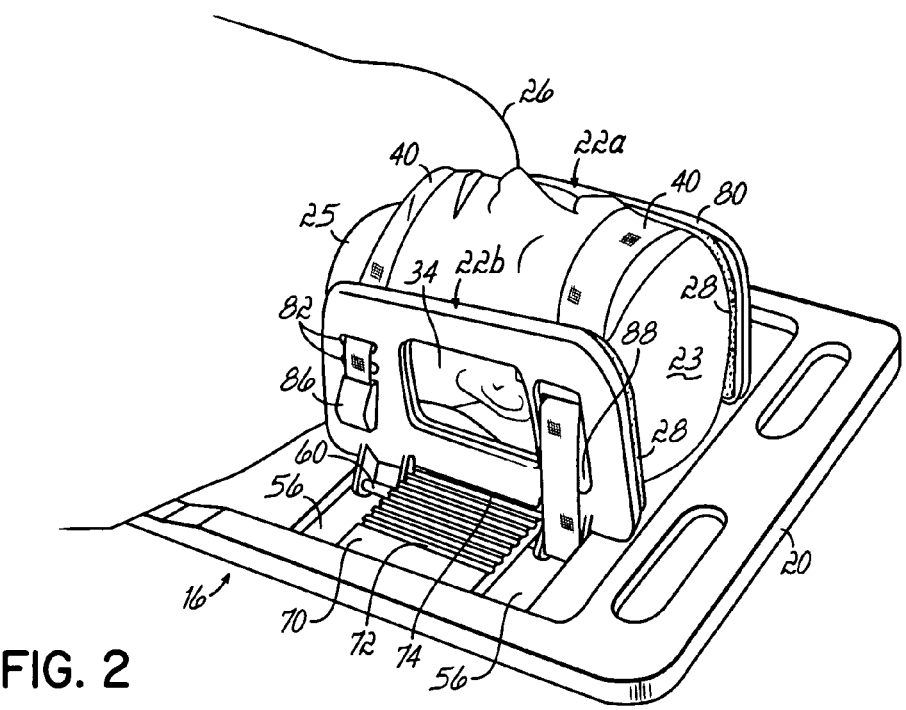
Figure 7:
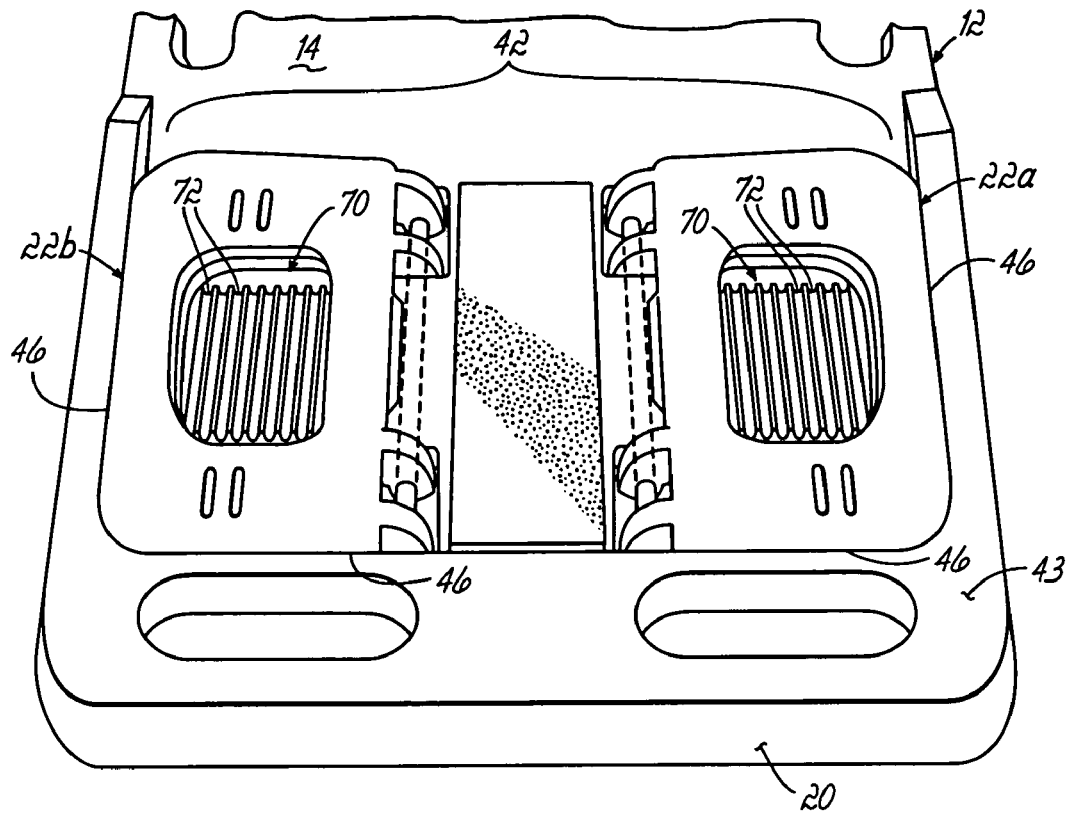
FIG. 7 is a perspective view of an embodiment of the invention illustrating paddles in the storage position.

Referring to FIG. 2, the head 23 and neck 25 of the patient 26 are secured and immobilized between the paddles during use. The body of the patient 26 lies along the length of the backboard 12, and often is secured to the backboard with straps, tape or other securement structures (not shown). As illustrated in FIGS. 1A, 1B, and 7, and discussed herein below, the paddles are movable between a support position or upright position, as illustrated in FIG. 1, and a storage position or flat position (see FIG. 7) for storing the device 10 when not in use.

The backboard 12 can be made out of wood, plastic, or any other suitable, and preferably light weight, material for supporting a patient with their head and neck immobilized between the paddles 22a, 22b.

The paddles may be made of a suitable rigid and light weight material, such as wood or plastic. For example, a polypropylene plastic, or high density polyethylene (HDPE) might be suitable. Paddles 22a, 22b include a layer or portion 28 of a conformable material for providing cushioning and comfort to the head 23 of the patient while providing a level of conformability to the paddles, for better securement and immobilization of the head and neck. For example, the layer 28 might be made of a conventional foam, such as a polyurethane foam, covered in a protective skin for cleanability. The protective skin 29 on the foam 28 provides an impermeable membrane for resisting the collection of bodily fluids and bacteria. Such a foam material is desirable both for its durability and its resistance to extreme temperatures and harsh chemicals, such as disinfectants.

To provide further comfort for an immobilized patient, a cushion 30 or a cushioned area between the paddles 22a, 22b might be used for cushioning the back of the head 23 of the patient. When a patient 26 is secured with the inventive device 10, as illustrated in FIG. 2, the backboard 12 may then be lifted utilizing hand holes 32, as are conventional with backboards.

Figure 3:
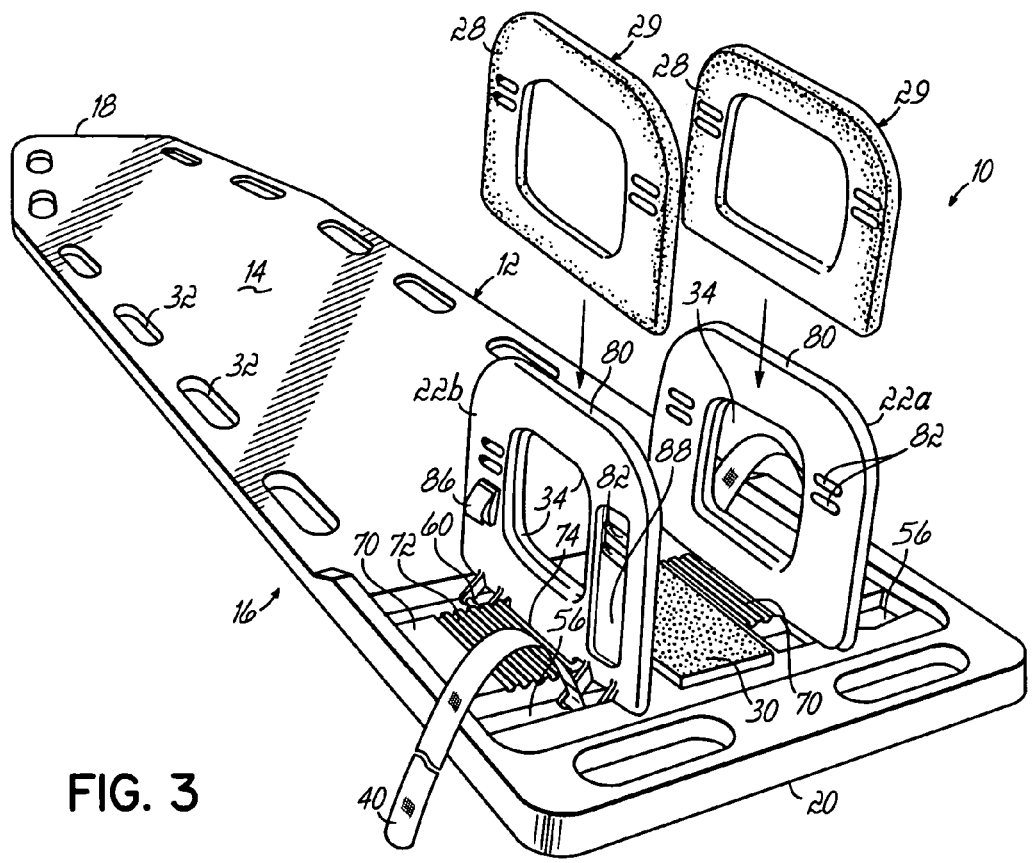
FIG. 3 is a perspective view of an alternative embodiment of the present invention.

Referring to FIG. 3, the layer 28 or layer material may be removable, such as for cleaning purposes. For example, the cushions 23 might be held to the paddles 22a, 22b by a suitable adhesive, by hook/loop fasteners, or by physically sliding the layers into tracks (not shown) formed within the paddles. Other suitable securement methods may also be utilized to removably secure the layers 28 with the paddles 22a, 22b. Preferably, the material utilized to form the paddles and any conformable layers 28 herewith is x-ray translucent so that x-rays may be taken with the patient in a stabilized position, as illustrated in FIG. 2.

The paddles 22a, 22b and associated conformable layers 28 have openings 34 formed therein so that the patient may hear better, such as for hearing instructions from a care giver or emergency medical personnel. Often overlooked during patient transport is the patient's ability to hear. The ear holes 34 are free from obstructions, thus decreasing the possibility of miscommunication with an injured patient.

Furthermore, the openings 34 allow visual inspection of the ears, or fluid coming from the ears, which is often indicative of head trauma. The ear holes, or openings 34, are placed to allow for greater visualization of a patient's ear. Ear holes 34 allow for better visualization and touch by medical personnel. In that way, they provide important diagnostic information about the type and extent of the injury by the type and amount of any fluid drainage of the ear. In one embodiment, the ear openings or ear holes 34 have an aspect ratio (i.e., the ratio of the depth or thickness of the paddle at opening 34 to the width or length of the opening 34), conducive to better hearing.

Figure 13:
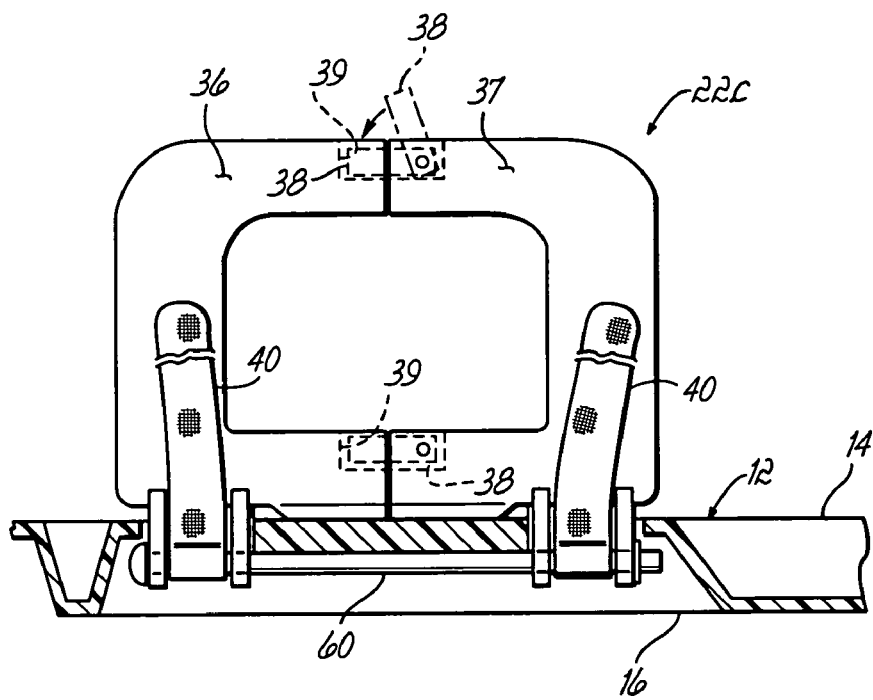
FIG. 13 is a side view, in partial cross-section, of another alternative paddle of the present invention.
Figure 14:
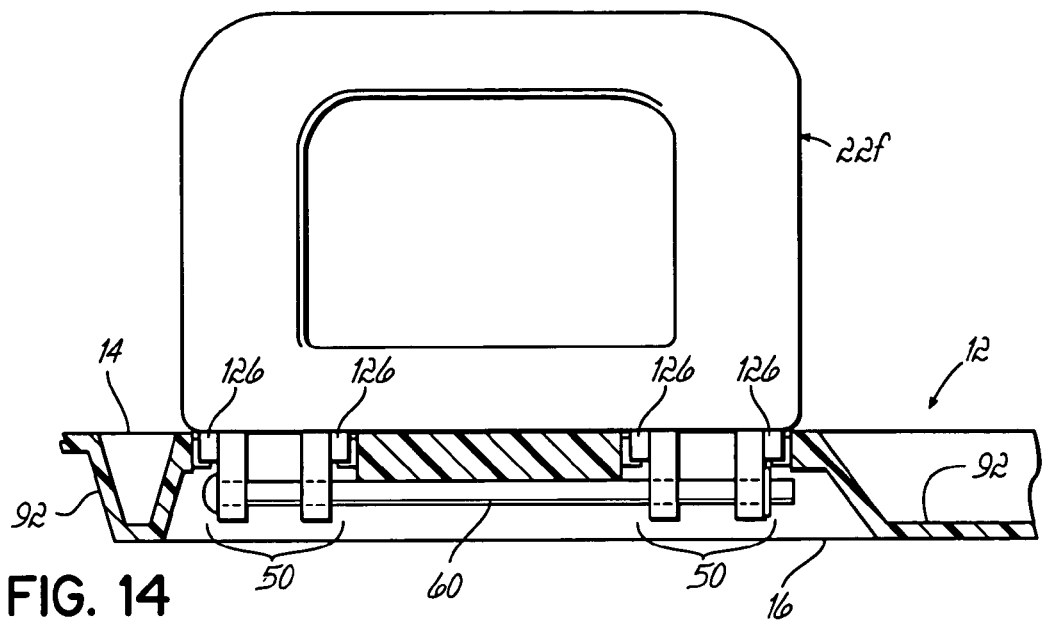
FIG. 14 is a side view, in partial cross-section, of an alternative embodiment of the present invention.
Figure 15:
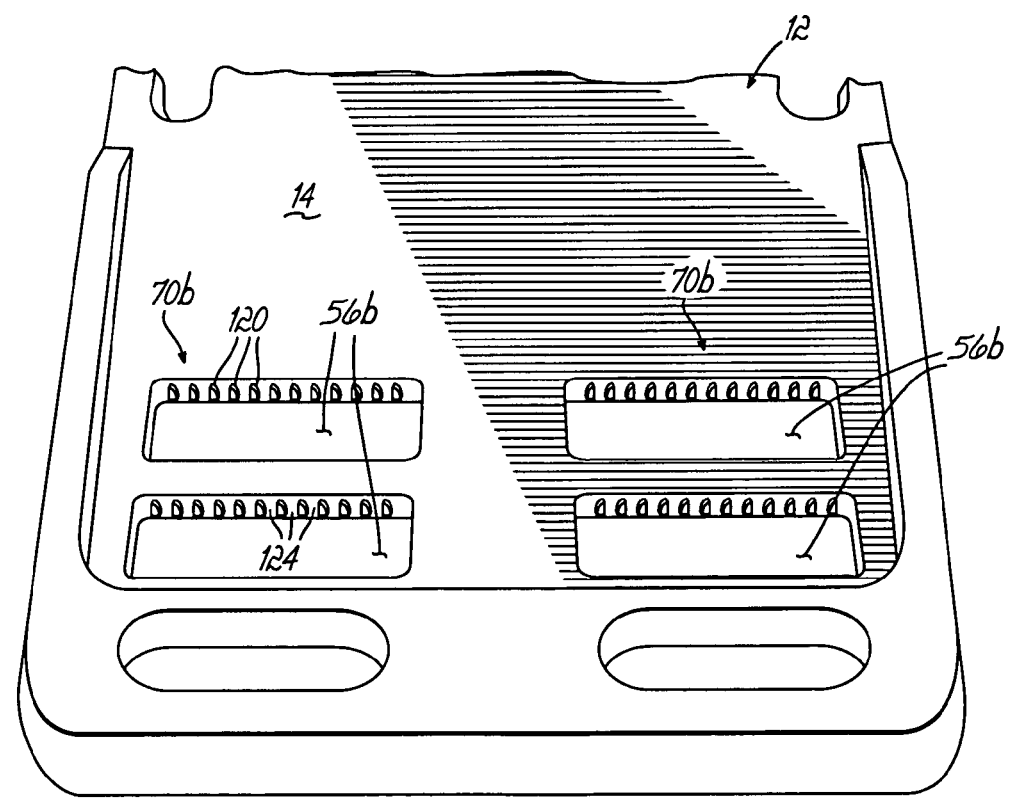
FIG. 15 is a perspective view of an alternative embodiment of the present invention, with the exemplary paddles removed for clarity.

In an alternative embodiment of the paddles, as illustrated in FIG. 13, the paddle might be split into multiple sections for visual and manual examination. One section is movable to a storage position to expose a portion of the head and/or neck while the other section remains in a support position to support the head and/or neck. Paddle 22c, FIG. 13, includes two sections: 36 and 37, which may be coupled together with a coupling structure such as a clasp, key, or other structure. For example, in FIG. 13, rotatable keys 38 are shown that rotate into appropriately formed key slots 39, formed in sections 36, 37. The keys 38 in slots 39 assure that the paddle sections stay together to form the unitary paddle 22c for immobilizing the head and neck of a patient. When it is desirable to physically examine the neck or part of the head, the appropriate section of paddles 22c may be uncoupled and folded to a storage position to allow access to a portion of the head or neck. The other section remains in the support position to continue to support the head and neck. Then, the section can be folded back up into a support position, and secured to form a unitary paddle 22c.

The shapes of the paddles, which are shown generally in a side view to resemble the shape of a "D" or "O", provides support for both the temporal and parietal areas of the skull, while also providing support for the zygomatic arch and any cervical collar utilized on the patient, as illustrated in FIG. 2. To secure the patient's head and neck between the paddles and to hold the paddles in a support position against the head and neck of the patient, one or more straps 40 or other securement structures are utilized. The straps span between the paddles, as illustrated in FIG. 2 and hold them in the support position. In accordance with one aspect of the invention, the straps 40 are integral with the device 10 and remain with it even when stored. In that way, the necessary straps are always with the device and do not have to be separately stored and retrieved. In the embodiment shown in FIGS. 1 and 2, one end of the straps is secured to the device 10, while a free end may be spanned between the paddles, based upon the width of the patient's head and the separation of the paddles. Securement, adjustability, and storage of such straps 40 are discussed herein below, in accordance with other aspects of the invention. Also, as noted below, other securement structures (i.e., tape, separate straps) might be utilized.

In accordance with one aspect of the present invention, the paddles 22a, 22b are secured to the backboard 12, and remain with the device 10 not only when in use, but also when it is stored. To that end, the paddles are movable from a support position, as illustrated in FIGS. 1 and 2, to a storage position, as illustrated in FIGS. 1A and 7. In one embodiment of the invention, the paddles are essentially rotatably mounted with respect to the backboard, and rotate between the storage positions and support about axes, which are generally parallel with the longitudinal axis of the backboard. Referring to FIGS. 1A, 1B, and 1C, the rotation of the paddles in one embodiment is illustrated. As discussed below, portions of the paddles, which extend through the board and along the back side, travel in a generally arcuate path between the storage and the support position. Referring to FIG. 7, in one aspect of the invention, the backboard, proximate the head end 20, forms a recess 42 to receive the paddles 22a, 22b in the storage position so that the paddles are generally flush with or below the front side surface 43 of the backboard proximate the head end 20. As is illustrated in FIG. 7, a raised area of the backboard is formed proximate to the head end to create such a recess to receive the stored paddles. Alternatively, the backboard 12 might be molded so as to form indents into the board to receive the paddles. For example, the entire thickness of the backboard might match that shown at the head end in the embodiment illustrated in FIGS. 1, 2, and 7 with a recessed area 42 formed therein for the paddles. The paddles 22a, 22b and the recessed area 42 may be appropriately configured and dimensioned to provide an interference fit for the paddles to keep them in the storage position until needed for use. For example, an interference or friction fit at the edges 46 of the paddle might keep them in the recessed area 42 until they are pulled upwardly to a storage position. Alternatively, some kind of latching or securement mechanism might be used to keep the paddles in place.

In accordance with another aspect of the present invention, the opposing paddles 22a, 22b are also slidably mounted with respect to the backboard to adjust their positions on the backboard. When the paddles are pulled up from the storage position and toward the support position, they may then be freely slid toward each other or apart to adjust to the width of the patient's head, neck, or any other medical gear or items attached thereto. Generally, in the storage position, the paddles are at 0 degrees with respect to the front side 14 of the backboard, or with respect to the overall plane of the backboard. In the support position, as illustrated in FIGS. 1 and 2, the paddles are approximately generally perpendicular to the front side 14 or to the plane of the backboard 12. Of course, the paddles may be angled somewhat from a perpendicular position, and it is not critical that they are at 90 degrees with respect to the plane of the backboard in the support position. In accordance with an aspect of the invention, the paddles are configured so that generally when they are oriented at an angle between the range of approximately 20 degrees to 70 degrees from the plane of the backboard, they may be slid freely together and apart for proper adjustment. Of course, angled outside this range, they may slide as well, just not as freely. Once in the support position or perpendicular position, they engage a respective index structure, as discussed herein below, to lock the paddles at a desired separation for support of the patient's head 23 and neck 25 as illustrated in FIG. 2.

Turning now to FIGS. 1A, 1B and 1C, the paddles include one or more leg portions 50 that extend or depend from the head-engaging section or body of the paddle. Referring to FIG. 1A, a cross-sectional side view of a paddle 22a is illustrated showing a leg portion 50 depending from a head-engaging portion or body 51 of the paddle. The leg portion 50 extends at an angle with respect to a plane 53 formed by body 51 of the paddle. In one embodiment, leg portion 50 extends generally approximately 45 degrees with respect to a plane 53 formed by paddle body 51. To accommodate and accept the leg portion or portion of the paddle, respective slots 56 are formed in the backboard proximate to each paddle and specifically proximate to the leg portions dependent there from (See FIG. 1). The number of slots may vary, as discussed below. For example, the embodiment illustrated in FIGS. 1 and 2 utilizes a pair of slots per paddle corresponding to the pair of leg portions depending from the paddles. The slots extend generally transverse to a longitudinal axis of the board.

Referring to FIG. 1D, two leg portions 50 are shown extending from paddle 22a. The paddles also include spanning portions 60 that depend from the leg portions and engage the backboard to secure the paddle with the backboard. In the embodiment illustrated in FIGS. 1, and 1A-1C, the spanning portion 60 of the paddle is in the form of a pin or dowel 60, which spans between the leg portions 50 of the paddle. In the embodiment of FIG. 1, the spanning portion 60 spans generally along the back side 16 of the backboard, securing the paddle to the backboard (See FIG. 8). Furthermore, as noted below, the spanning portion 60 prevents the various paddles from being over-rotated in the support position so that they continue to remain at their desired support angle (e.g. 90 degrees) and to support the head and neck of a patient even when the backboard is turned on its side.

The spanning portion 60 of the paddle, such as the dowel or pin illustrated in FIGS. 1A-1C, allows the paddle to be moved transversely on the backboard to space the paddles apart or to move them closer together to accommodate the patient. When the paddles are rotated upwardly from the storage position (FIG. 1A) and generally upwardly through a range of approximately 20 degrees to 70 degrees above the plane of the backboard (FIG. 1B), the paddle may slide freely transversely on the board as illustrated by arrows 62 in FIGS. 1A, 1B. As shown in FIG. 1C, when the paddle is moved to the support position, the spanning portion 60 engages the backboard, such as by engaging the back side 16 of the backboard, and along with other portions of the paddle, prevents the paddle from being over-rotated in the direction of arrow 64 significantly past a desirable support position, such as a generally perpendicular position. In one embodiment, it is desirable that the paddle is prevented from movement beyond approximately 20 degrees from the perpendicular or beyond approximately 110E. Of course, the paddles might be confined even closer to the perpendicular, like under approximately +10 degrees or +5 degrees from that position. The spanning portion is held into position by the leg portions 50 of the paddle, which have appropriate openings formed therein. That is, the dowel in the illustrated embodiment is a separate part slid into appropriate openings formed in the leg portions. The dowel has a head 55 (See FIGS. 1C, 8) to secure it at one end. The spanning portion or dowel is then locked into place by securing the other end of the dowel with clips or other structures 57 (See FIGS. 1C, 8). Alternatively, the spanning portion might be integrally formed with the leg portions of the paddle to span between the leg portions and secure the paddle with the backboard. Again, although two leg portions are shown for each paddle, a greater or lesser number of leg portions may be utilized with suitable spanning portions for engaging the backboard to secure the paddle to the backboard. As noted, spanning portion may be integral with the leg portions, such as being molded with the leg portions. In the embodiment of the paddle as illustrated in the Figures, the leg portions are generally molded or formed integral with the paddle which as being molded with the paddle. Alternatively, they might be separately formed similar to the spanning portion 60, then secured to the paddle body 51. Preferably, any securing structures such as screws or bolts, which couple portions of the paddle together, are x-ray translucent.

In accordance with one aspect of the invention, in order to provide the necessary clearance between the spanning portion 60 and the paddle body 51 for the purposes of movement of the paddles closer together or further apart, the spanning portion moves in a generally arcuate path between the storage and support positions. Referring to FIGS. 1A, 1B, and 1C, in the storage position, the spanning portion 60, such as the dowel, rests against the back side 16 of the backboard. Generally, friction, and the engagement of the paddle body 51 and spanning portion 60 against the sides of the backboard, prevents or hinders movement of the paddle laterally on the board when it is in a storage position and the backboard is stored. When the paddle is folded up or hinged up toward the support position, as illustrated in FIG. 1B, the spanning portion 60 travels a generally arcuate path away from the back side 16, and then again toward the back side 16 when the paddle is locked in the support position, as illustrated in FIG. 1C. That is, as illustrated in FIG. 1B, movement of the spanning portion along the generally arcuate path 63 moves the spanning portion 60 away from the back side 16 to allow for lateral movement of the paddles, such as in the direction of arrow 62. The spanning portion is disengaged from the backboard and the paddle is free to move or slide. Such generally arcuate movement of the spanning portion provides for easy adjustment of the paddles when they are between the storage and support positions. The arcuate path also ensures that the spanning portion subsequently engages the back side of the backboard to ensure that the paddles are held appropriately or locked in their storage and support positions. Usually, depending upon the positioning of the paddles, the spanning portions 60 will not take a purely arcuate path, as illustrated in FIG. 1B, because the paddles will also be moved laterally, once they are out of the storage position. For example, the spanning portion 60 might move arcuately to the position illustrated in FIG. 1B, and then might move in a linear fashion (arrow 62) as the paddles are adjusted to their proper widths for supporting the head and neck of a patient. Then, as the paddles are moved the rest of the way up to the storage position, as illustrated in FIG. 1C, a generally arcuate path might again be traversed by the spanning portion 60. Therefore, as used herein, the term "generally arcuate path" does not require that the arc be continuous, but only that the spanning portion move away from the back side of the backboard and then back toward that back side for movement between the storage and support positions.

Figure 8:
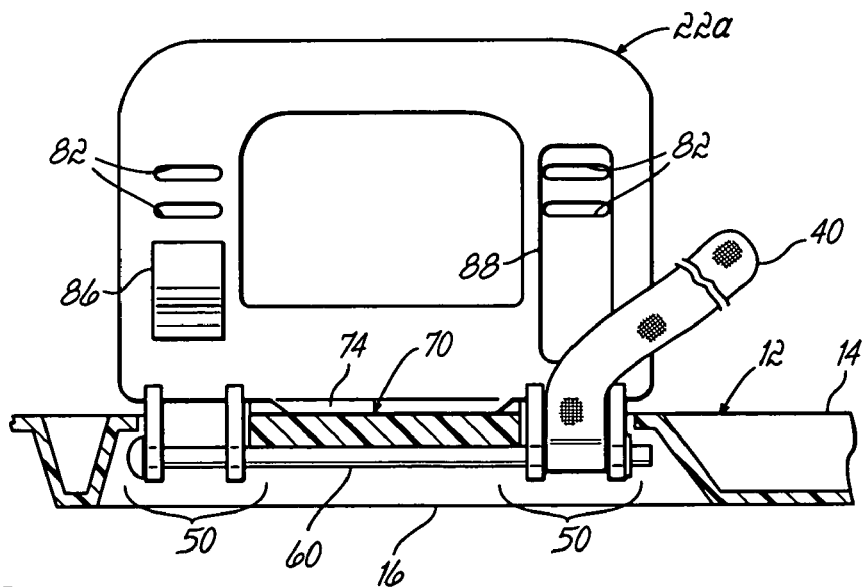
FIG. 8 is a side view, in partial cross-section, of a paddle of the invention in the support position.

Referring to FIG. 8, a side view of the paddle is shown, in partial cross-section, wherein the paddle is in the support position. As illustrated, the spanning portion 60 spans between the leg portions 50 and engages a portion of the backboard, such as the back side 16 of the backboard to secure the paddle and prevent the paddle from rotating in a storage position generally beyond perpendicular or some other desired angle. In accordance with one aspect of the present invention, the spanning portion engages the backboard when the paddle is moved to the support position and restricts movement of the paddle in the support position significantly beyond 90 degrees from the plane of the backboard. Preferably, in the illustrated embodiment, the spanning portion 60 maintains the paddle generally close to perpendicular. In that way, the neck and head of a patient are maintained in a desirable position on the backboard when the backboard is moved, and particularly when it is turned on its side. As may be appreciated, with the head secured between the paddles, such as with straps 40, turning the backboard 12 on its side, such as to move the patient between a doorway or some other opening, puts significant stress upon the upper portions of the paddle pair because the weight of the head cantilevers from that paddle. In the present invention, with the paddles prevented from rotating in the support position significantly beyond perpendicular or 90 degrees; this ensures that proper immobilization of the head and neck is maintained during movement of the patient. Generally, when the straps 40 are secured into position snugly on the head and neck of a patient, the paddles will be secured in a generally perpendicular position, ensuring full contact between the sides of the paddles and the head and neck of the patient. Proper utilization of the securement straps and proper positioning of the paddles on the sides of the head ensure that the paddles will generally not be less than approximately perpendicular or 90 degrees from the plane of the backboard.

In accordance with another aspect of the present invention, in the support position, the paddles are locked into position at the proper spacing, utilizing index structures that are engaged by the paddles. The paddles generally engage their respective index structures when the paddles are moved to the support position and thereby are locked relative to each other to support a patient's head and neck. Preferably, they are locked in a position that is centered about the center of the longitudinal axis of the backboard so that the patient's head and neck are centered on the backboard with the patient.

Referring to FIG. 1, index structures 70 are illustrated positioned on a front side of the backboard. The index structures 70 of FIG. 1 are in the form of a plurality of grooves (See FIG. 7), which extend longitudinally with respect to the backboard's long axis. The grooves 72 define various index points along the index structure for positioning of the paddles 22a, 22b. The grooves 72 may be formed as individual index structures for each paddle, as illustrated in the Figures. Alternatively, they may be part of a continuous index structure with a portion of the index structure being utilized for each respective paddle. The embodiment in FIG. 1 shows two individual index structures 70, one for each paddle. The index structures are positioned proximate a side of the slot or slots.

The index structures, such as grooves 72, may be integrally formed with the backboard 12, such as by being molded as part of the backboard. Alternatively, the index structure or structures might be separately formed and then secured to the backboard. For example, the grooves 72 might be formed in a plate that is then fastened to the backboard, such as with screws or other fasteners. While the grooves 72 are shown somewhat elongated to engage in an elongated, protruding ridge 74 of the paddles, as discussed below, they might be shortened to essentially form indents. The protruding ridge 74 would then be appropriately shortened to essentially form a knob to engage the indent and secure the transverse or lateral spacing of the paddles 22a, 22b.

To lock the paddles into position with respect to each other and to prevent them from being spread apart when the head and neck of the patient has been immobilized, a portion of the paddle engages the respective index structure. Specifically, in an embodiment illustrated in FIGS. 1 and 1A-1C, a protruding ridge 74 engages a respective groove 72 of the index structure 70. Referring to FIGS. 1A and 1B, when the paddle is moved from the storage position and is positioned generally in the range of 20 degrees to 70 degrees above the plane of the backboard, the spanning portion 60 and the ridge 74 of the paddle are not forced to engage the backboard and the grooves 72, respectively. That is, they are double open-ended grooves. In that way, the paddle slides freely in the direction of arrow 62 (see FIG. 1A) to the proper position, such as close to the neck and head of a patient lying on the backboard. At the proper position the paddle can be moved or rotated completely upwardly to the support position, which, for example, may be generally perpendicular to the plane of the backboard. At that time, the spanning structure 60 is forced into engagement with the backboard such as the back side 16 of the backboard, and the ridge 74 meets and slides into a particular groove 72 to lock the paddle at an index point on the index structure. As illustrated in the cross-section of FIG. 1B, the ridge 74 seats within the respective grove 72 when the paddle is in the support position. The engagement of the index structure by the paddle in that way laterally locks the position of the paddle so that it cannot be moved apart from the opposing paddle. With both the paddles in the support position and locked in such a way, the width or spacing between the opposing paddles for accommodating the head and neck of the patient is fixed. The present invention may accommodate a wide variety of head widths, ranging from pediatric to adult, even up to a patient with a helmet, such as a motorcycle helmet, on their head.

As illustrated in FIG. 1, the ridge 74 is dimensioned to generally span the length of the grooves of index structure 70 to provide proper securement of the paddles in the proper position. The spacing between the various index grooves 72 and the length of the grooves and the ridge 74 may be varied depending on the desired spacing of the indexing points and the robustness of the paddles and their securement. When the paddles are moved to the vertical or support position with respect to the backboard, the protruding ridges 74 are preferably configured to fit somewhat snugly into the grooves 72. This allows the paddles to freely stand up in a support position while simultaneously locking the transverse position of the paddles on the backboard. The straps 40 can then be applied to span the head and neck of the patient and between the opposing paddles as illustrated in FIG. 2.

In accordance with another aspect of the present invention, it is desirable that a backboard, particularly the head and neck restraining portion of such a backboard, be readily and easily cleanable. Prior art backboard and prior art head/neck immobilization structures have provided a plurality of cavities and recesses in which blood or other bodily fluids might collect when in use. To then clean and sanitize the structures for the next use, medical personnel must painstakingly scrub the structures and get into the various cavities to reduce the risk of transmission of fluid and blood-borne pathogens and contamination of a subsequent patient. In the present invention, the grooves 72 are open at their ends and open into the respective slots 56, as illustrated in FIGS. 1, 2, and 7. In that way, the grooves can be wiped clean without any corners or walls for catching fluids. That is, the contents of the grooves can be wiped into the slots 56, which are open and therefore subject to easy cleaning. Alternatively, a fluid such as water or a disinfectant can be sprayed down into the grooves and will easily flow out the open ends and into the slots 56, and thereby off the backboard.

Figure 6:
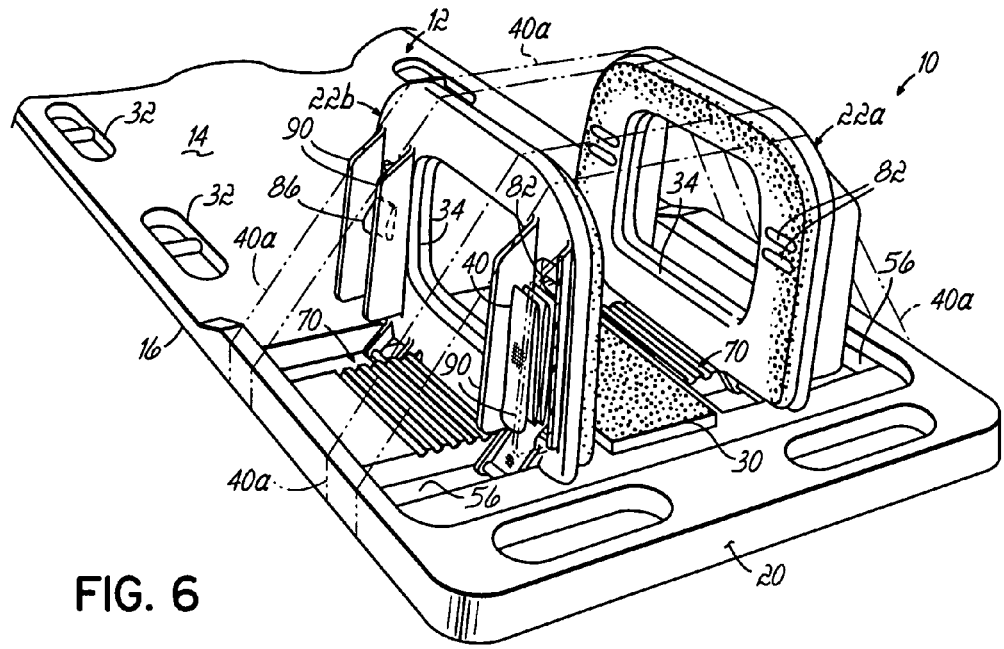
FIG. 6 is a perspective view of an alternative embodiment of the present invention.

To secure the paddles together in a support position to support a patient's head and neck, straps 40 may be utilized to span between the paddles and over a patient's head and neck, as illustrated in FIG. 2. Referring to FIG. 6, such straps may be made of tape 40a that span across the top edges of the paddle and are secured to the edges of the backboard in the typical securement methodology. However, by spanning tape across the top edges 80 of the paddle, the height of the securing straps or tape 40 is set by the height of the paddles. This may not provide desirable securement of the patient's head and neck, particularly for smaller patients such as infants and toddlers whose heads will be significantly below the height of the edges. In accordance with another aspect of the present invention, the strap 40 is adjustable in height on the paddle to adjust to different head height. Referring to FIGS. 1 and 2, openings 82 are formed in the paddles to receive the straps 40 at different heights on the paddle. Two such vertically spaced openings 82 are shown in the embodiment of the Figures. However a greater number of openings may be utilized for adjustment purposes. In that way, rather than spanning over the top edges 80 of the paddles, the straps 40 extend through the paddles and there across to span across the patient's head as illustrated in FIG. 2. The corresponding openings 82 are formed in each paddle for each strap utilized. In the illustrated embodiment, two straps are utilized, one at the forward end of the paddle (closest to the patient's forehead) and one at the rearward end of the paddle (closest to the patient's chin). The ends of the straps may be coupled to the backboard in any suitable fashion.

In the disclosed embodiments, a single strap is secured to each paddle and is secured with that paddle. The strap then spans across to the other paddle and is secured into position with an appropriate fastening technique. Referring to FIGS. 1 and 2, an end of the strap 40 is shown secured at a leg portion. Specifically, referring to FIG. 1C, the leg portions 50 are split into separate sections to allow the strap 40 to be secured around the spanning portion 60 that engages the leg portion 50, such as a dowel or pin. For example, the strap end might be slid around the dowel and be sewn. For immobilizing the head and neck, the free end of the strap is placed through the desired openings 82 in the paddles, over the head and neck of the patient, and through similar openings in the other paddles. As illustrated in FIG. 2, multiple straps, one on the forehead, and one proximate to the chin, might be utilized. The free end of the strap is then secured with an appropriate method, such as with adhesives, a buckle, hook/loop fasteners, or other securing mechanisms. In the illustrated embodiment, a cam buckle 86 is utilized to receive the free end of the strap 40.

Therefore, in accordance with one aspect of the present invention, the strap is integral with the immobilization device 10 and is stored with the backboard along with the paddles 22a, 22b to be readily available for use. Therefore, precious time is not wasted in securing paddles or blocks to the board and then securing the head between the paddles and block such as with separate tape or strap structures. While the straps 40 are shown secured to opposite paddles, they might be fixed to the same paddle with both free ends extending over to the other paddle.

The present invention contemplates storage of the straps with the paddles in the storage position. In accordance with another aspect of the present invention, the paddles are configured for storing the straps out of the way when the paddles are in the storage position. In one embodiment, as illustrated in FIGS. 1, 2, and 3, an indent 88 is formed in the back of the paddle for receiving a folded strap. When the paddle is then folded to the storage position, an interference fit keeps it within the paddle to keep it out of the way to prevent it from being caught during storage of the immobilization device 10. Alternatively, as illustrated in FIG. 6, raised walls 90 might be utilized to capture the strap 40 to secure it in an interference fit when the paddles are in a storage position. Therefore, once the strap is folded and loaded into the paddle, it is prevented from becoming loose by a tight interference fit.

An alternative embodiment of the invention is illustrated in FIG. 3. Layers 28 utilized with the paddles 22a, 22b may be removable for being disposable, or disinfected and reused. For example, they might be fastened by a suitable adhesive or hook/loop fasteners to be readily pulled away from the paddles after each use and discarded. Alternatively, they might slide into tracks or otherwise engage paddles 22a, 22b to be easily removed and replaced after each use so that the layer does not need to be cleaned. Referring to FIG. 13, if the paddle is split, a suitably split cushion is utilized to allow the separate sections of the paddle to be separated as desired.

Figures 4, 5:
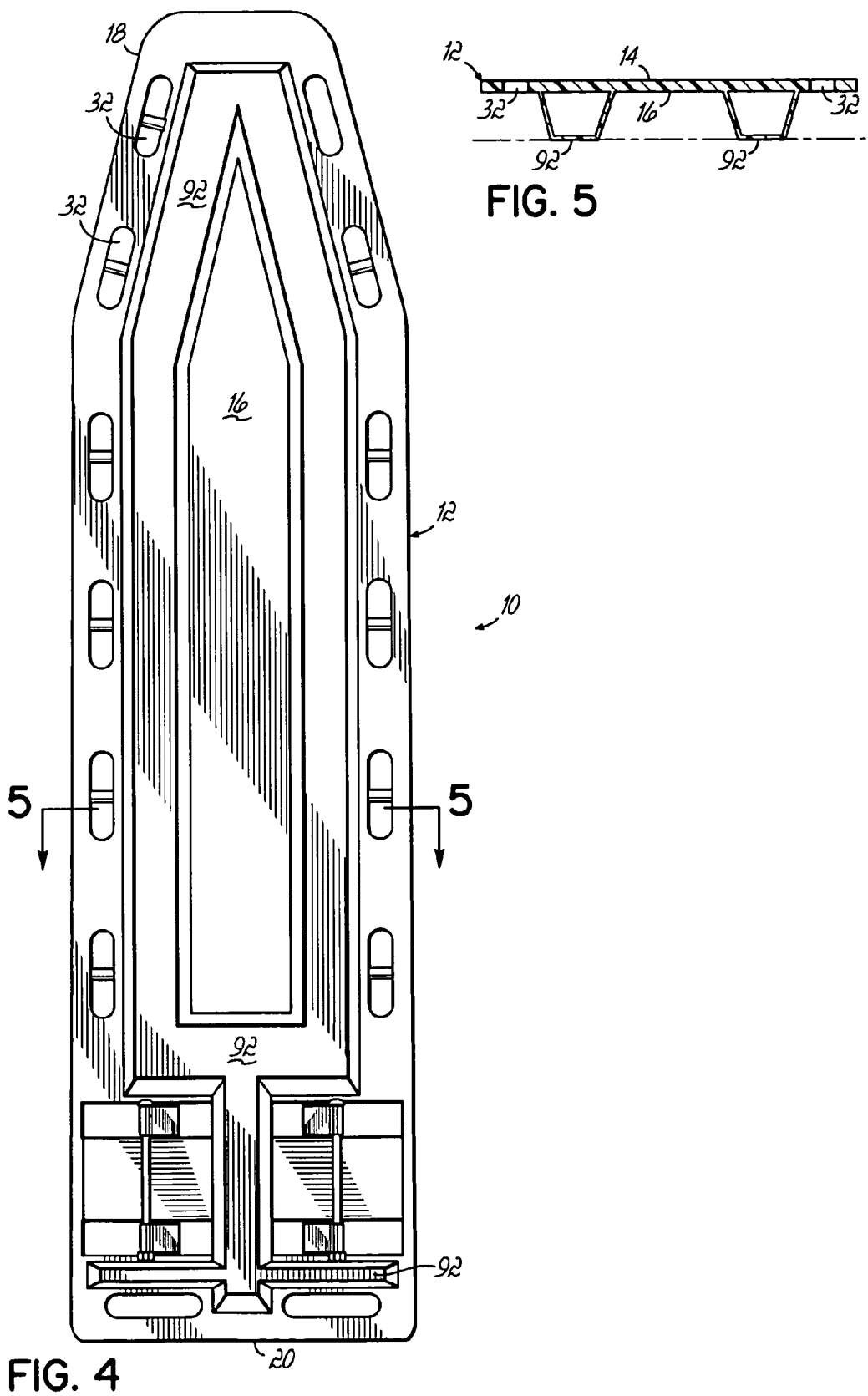
FIG. 4 is a bottom plan view of one embodiment of the backboard of the present invention.
FIG. 5 is a cross-sectional view along lines 5-5 of FIG. 4.

FIGS. 4 and 5 illustrate another aspect and embodiment of the present invention, which facilitates grasping and lifting the backboard by medical personnel, and also ensures sufficient operation of the paddles when they are adjusted. Referring to FIG. 4, the backboard 12 includes a network of raised areas 92 along the length of the backboard and also proximate the head end 20 of the backboard. The raised areas elevate the hand holes 32 off the ground to allow medical personnel to easily slide their hands underneath the backboard to lift a patient secured thereon. Generally, the hand holes 32 will be placed equidistant along the border of the backboard 12 to promote balance while carrying the patient. The raised areas might be formed by securing appropriate ridges to the back side of the backboard. Alternatively, such raised areas may be molded with the backboard, such as when the backboard is made out of a suitable plastic material. In accordance with another aspect of the invention as illustrated in FIG. 4, the hand holes 32 might include pins that span the holes and are configured for strapping to clips or straps such as for strapping a patient onto the backboard.

The raised areas 92 proximate the head end 21 provide proper clearance for movement of the leg portions 50 and spanning portion 60 of the paddles. Turning again to FIGS. 1A, 1B, clearance for the lateral adjustment of the paddles is necessary so that the leg portions and spanning portion are not hindered. Similarly, interference between the paddle and a ground or support surface is prevented so the paddles may be readily moved between storage and support positions.

Figure 9:
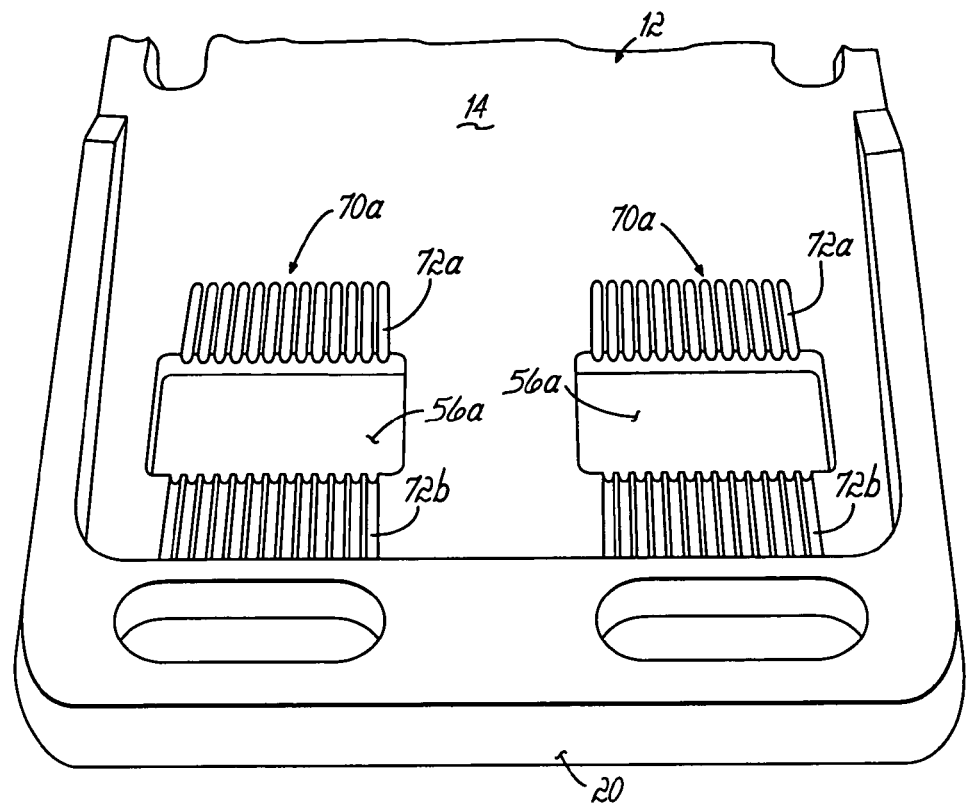
FIG. 9 is a perspective view of an alternative embodiment of the present invention.
Figure 10:
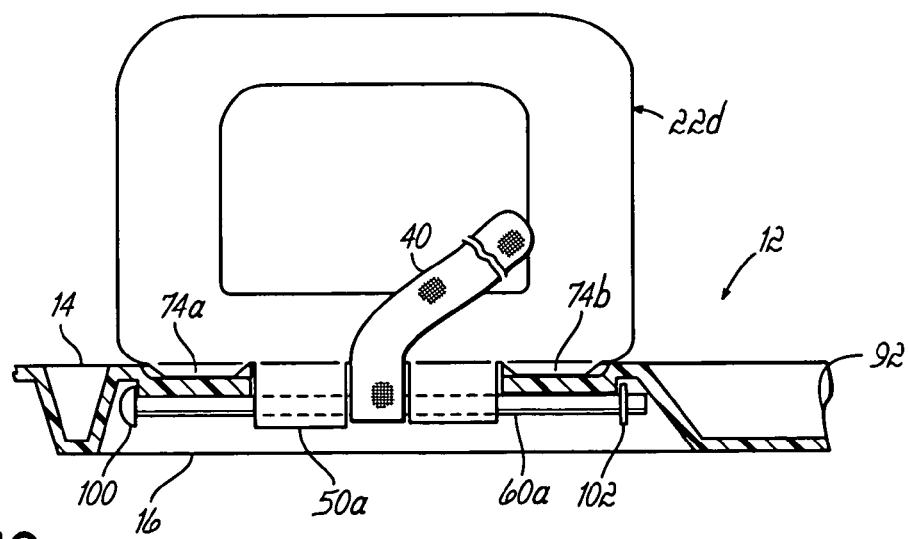
FIG. 10 is a side view, in partial cross-section, of an alternative embodiment of the invention illustrating the paddle in the support position.

FIGS. 9 and 10 illustrate an alternative embodiment of the invention, in which a single slot 56a is utilized rather than multiple slots, while the index structure is in the form of a plurality of grooves 72a, 72b positioned on either side of the slot 56a. That is, the index structures 70a, rather than spanning between two slots, is positioned on either side of the single slot 56a. FIG. 10 illustrates a paddle 22d that engages slot 56a and the index structure 70a. The protruding ridge is divided into two sections 74a and 74b, for engaging the respective grooves 72a and 72b in the index structure when the paddle 22d is moved to the support position as illustrated in FIG. 10. Paddle 22d includes a single leg portion 50a that engages the slot 56a. The spanning portion 60a of the paddle 22d spans to either side of a leg portion 50a to secure the paddle to the backboard. In the embodiment illustrated in FIG. 10, the spanning portion is in the form of a pin or a dowel that extends through an appropriate opening formed in the leg portion 50a and spans along a back side of the board generally below the grooves 72a, 72b of the index structure. The pin or dowel is held into position on one side by a head 100 and on the other side by a clip 102. Alternatively, as noted above, the spanning portion might be integrally formed with the leg portion 50 or the paddle 22d, such as by being molded with either of those components.

Figure 11:
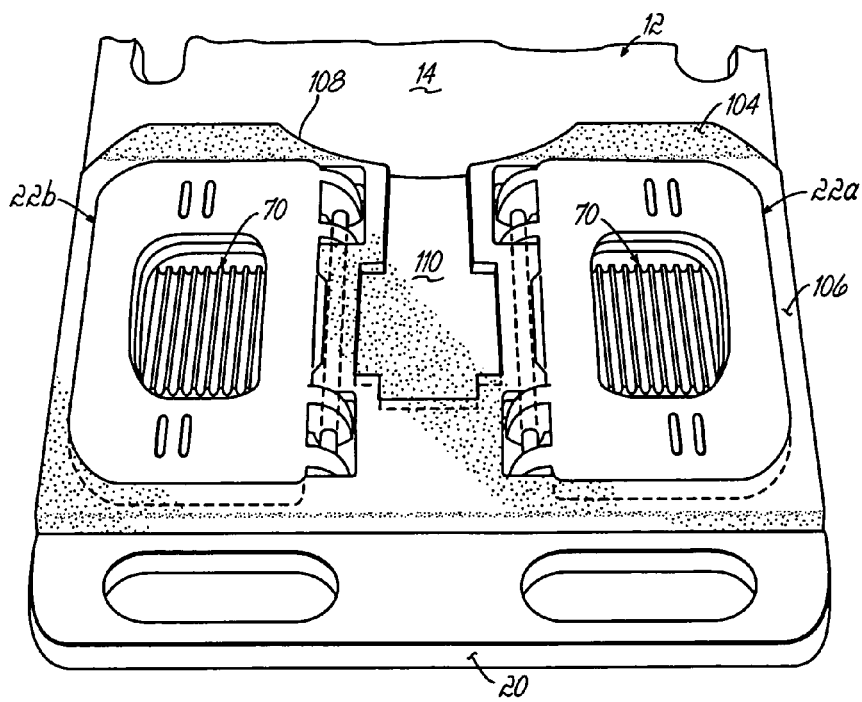
FIG. 11 is a perspective view of an alternative embodiment of the present invention with paddles in the storage position.

FIG. 11 illustrates an alternative head end for an immobilization device of the present invention. The paddles utilized are similar to those illustrated in FIG. 1, although they could be any suitable paddles, included those illustrated herein. The head end 20 of the backboard in FIG. 11 utilizes a raised area 104 that has recessed areas therein 106 for receiving the paddles 22a, 22b in the storage position. The raised area tapers at a rearward edge 108 down to the front side of the backboard. In that way, the raised area 104 defines an area for supporting the head of a patient and also demarcates a position at the rearward edge 108 for positioning the shoulders of a patient. That is, at the tapered demarcation provided at the rearward edge 108, the medical personnel have a reference point for sliding the patient's body along the board for proper alignment of their head with the paddles. Because of different physiologies among patients, the edge 108 does not provide an exact point, but rather offers a reference point between the paddles. To receive the head, an indent portion 110 is formed to allow the head to nest between the paddles 22a, 22b. The raised portion might be formed as a separate piece attached to the front side 14 of the boarded or it might be molded integrally with the board. The indent portion 110 in one embodiment includes a suitable cushion material, similar to cushion 30, as illustrated in FIG. 1.

Figure 12:
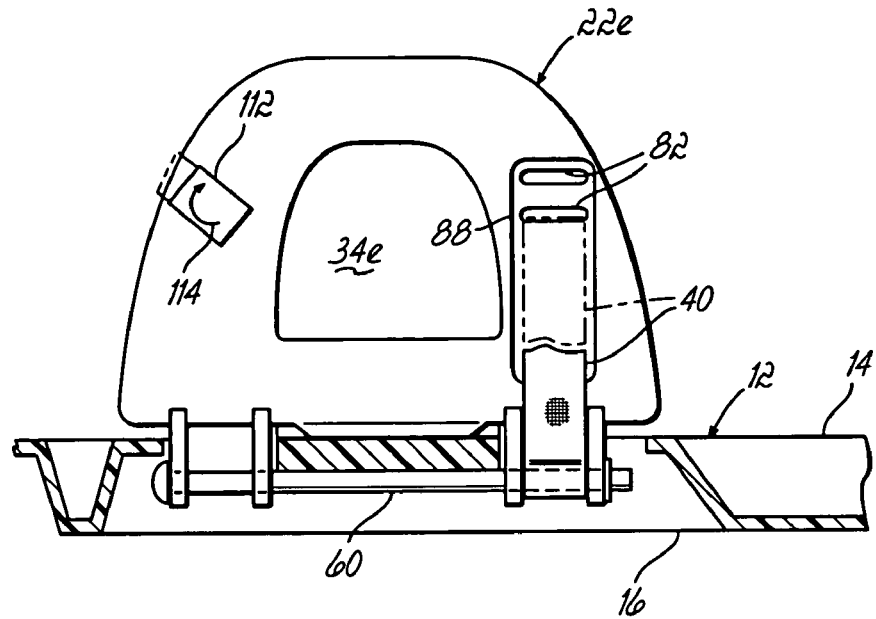
FIG. 12 is a side view, in partial cross-section, of an alternative paddle of the present invention.

FIG. 12 illustrates an alternative embodiment of a paddle 22e in which the height of the paddle is raised to provide a wider and taller ear hole 34e. Paddle 22e is configured to have an indent area 88 therein for storing the strap 40. Furthermore, the paddle has openings 82 for positioning of the strap along the height of the paddle to adjust to different patient heads. To receive the free end of the strap 40, such as from the other paddle, a buckle, such as a cam buckle 112 or other attachment device is utilized and is rotatable about a center axis as illustrated by arrow 114. The other end of strap 40 is secured, such as by coupling with spanning portion 60.

FIGS. 14-17 illustrate further alternative embodiments of the invention, and particularly illustrate an alternative index structure for locking the paddles at certain indexed positions on the backboard. Rather than being positioned on the front side of the backboard, the index structure is incorporated into slots formed through the backboard. Specifically, with respect to FIG. 14, a paddle 22f is shown and is somewhat similar to other paddles discussed previously, such as those shown in FIGS. 7 and 8. Therefore, like numerals are utilized where possible for similar components between the embodiments.

Figure 16:
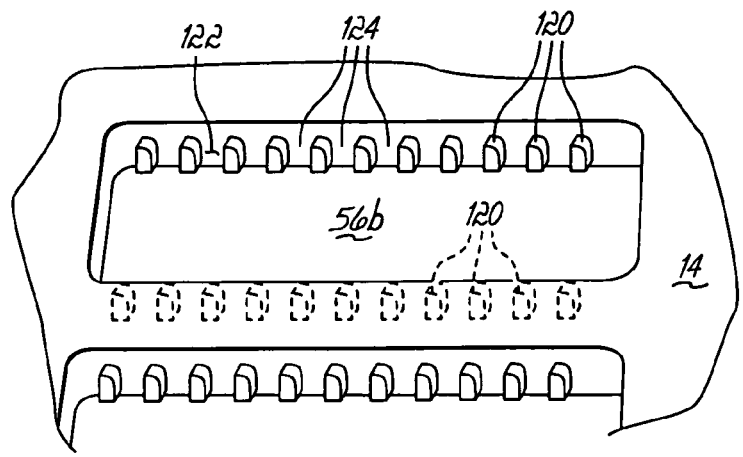
FIG. 16 is a partial cut-away perspective view of an alternative index structure of the present invention.

The index structure 70b includes a plurality of posts 120 that extend into slots 56b formed in the backboard. As illustrated in FIG. 16, two sets of posts in an opposing relationship extend into the slots 56b from a side wall 122 of the slots. The posts provide index channels 124 there between into which corresponding index tabs 126 slide when the paddles 22f are in the support position (see FIG. 14). Therefore, the posts 120 provide an index structure 70b for indexing the paddle 22f at desired positions to provide for proper spacing between the opposing paddles to secure and immobilize the head and neck of a patient. Similar to the paddles discussed above, the paddle may be freely movable when raised to a position between the storage position and the support position and will slide transversely with respect to the slots 56b to vary the space between the opposing paddles. When the paddles are moved to a generally perpendicular support position and the spanning portion 60 of the paddle engages the backboard, the index tabs 126 engage the index posts 120 in the slots 156b. More particularly, the index tabs 126 slide into the channels 124 created between the index posts. The embodiments illustrated in FIGS. 14-17 further enhance the cleanability of the immobilization device of the invention by eliminating any cavity that catches fluid. Any fluid proximate to slots 56b and the paddles 22f and specifically fluid contacting the index structures 70b will be able to pass over the slots and various posts 120 that form the open channels 124. In that way, water or other fluid may be directed down through the channels 124 and around the posts to keep them clean of blood or other bodily fluids.

Figure 17:
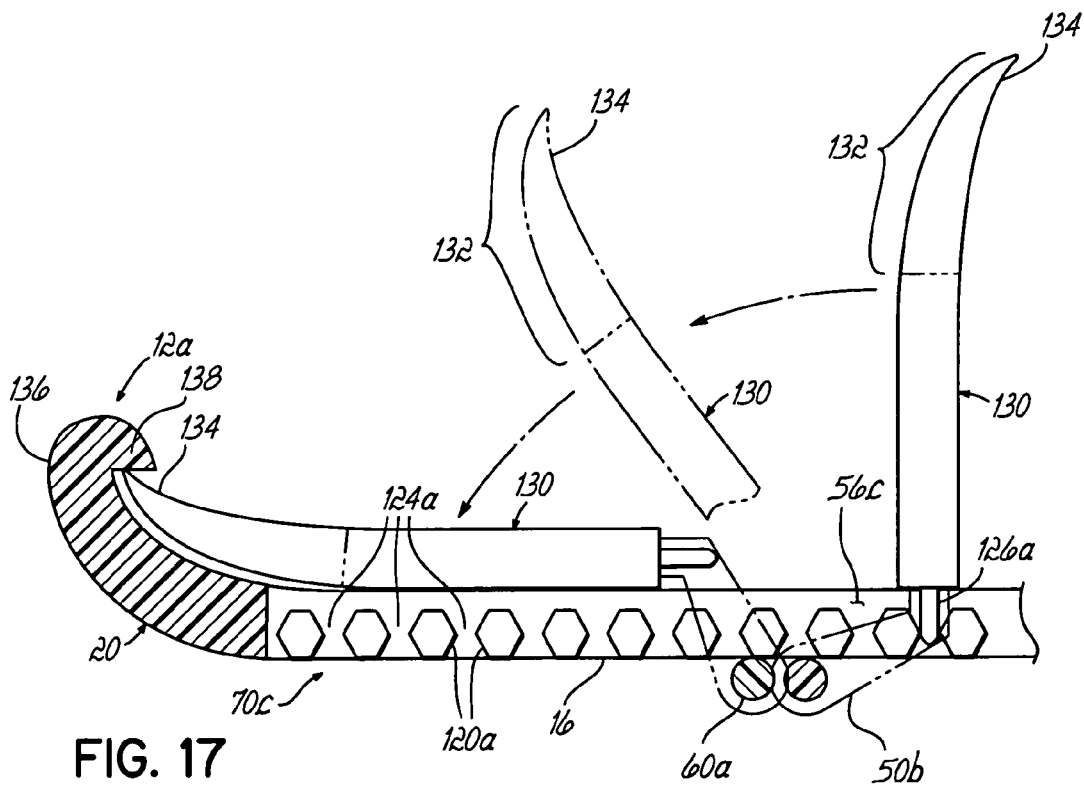
FIG. 17 is a partial cross-sectional view of an alternative embodiment of the invention.

FIG. 17 illustrates another alternative embodiment of the invention and shows a cross-sectional view of a backboard and paddle shaped for more closely conforming to the head of a patient. Specifically, paddle 130 is not generally similar to other paddles discussed herein above. Rather, the paddle has a concave shape toward the head and neck of a patient to provide better conformity around the head of the patient. The top 132 of the paddle 130 has a concave shape that will more closely conform to the side of the head of a patient. Paddle 130 may be made of a pliable material such as a plastic or hard rubber material that will allow it to more closely conform to a patient's head when in the support position. Straps, tape or other securing structures spanning between the opposing paddles 130 will secure the paddles in the support position and will more closely conform the paddles to the patient's head and neck. In one embodiment, the entire paddle may be formed of pliable material. Alternatively, the paddle might include a pliable tip section 134 that will provide conformity generally where the paddle engages curved portions on the side of a patient's head or neck. In another aspect of the invention, as shown in FIG. 17, the side of the backboard, proximate the head end 20 where the paddles are located, is formed to hold the conformable paddles 130 in the storage position. As illustrated in FIG. 17, the backboard 12a includes a side section 136 with an overhang 138 that captures the top portion 134 of the paddle. The compliant paddle may then be pulled from a storage position and out from the overhang 138 to be moved to the support position as illustrated in FIG. 17. Paddle 130 includes one or more leg portions 50b, which extends through slots 56c formed in the backboard. A spanning portion 60a secures the paddle 130 with the backboard and provides a stop mechanism for the paddle in the support position to prevent over-rotation, as discussed above. In the embodiment of FIG. 17, an index structure 70c includes a plurality of posts 120a at index positions along the width of the board. Index tabs 126a on the paddles 130 engage channels 120a formed between the index posts 120a to laterally or transversely secure the paddle in a specific indexed position corresponding to a particular width of the head and neck of a patient. The embodiment of FIG. 17 also provides the benefit of open channels 124a that do not collect bodily fluids and associated blood/fluid-borne pathogens. The paddles 130 may be secured around the head and neck of a patient such as with straps, tapes, or other securement structures. Furthermore, the paddles 130 may have other features such as ear holes and strap storage components similar to those in the embodiments discussed above.

Figure 18:
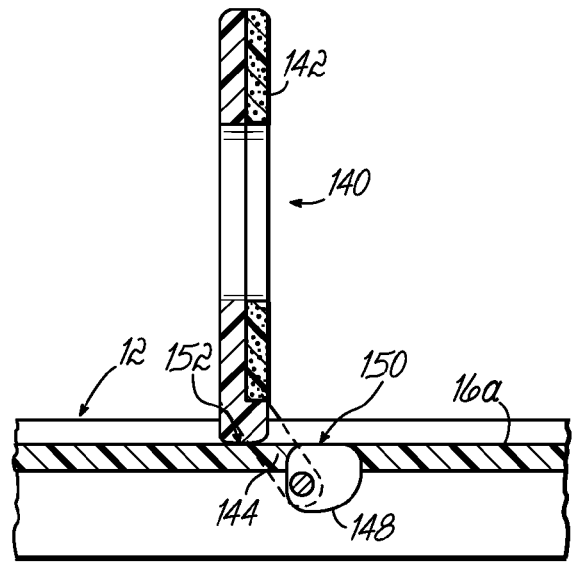
FIG. 18 is an end cross-sectional view of another embodiment of the invention.
Figure 19:
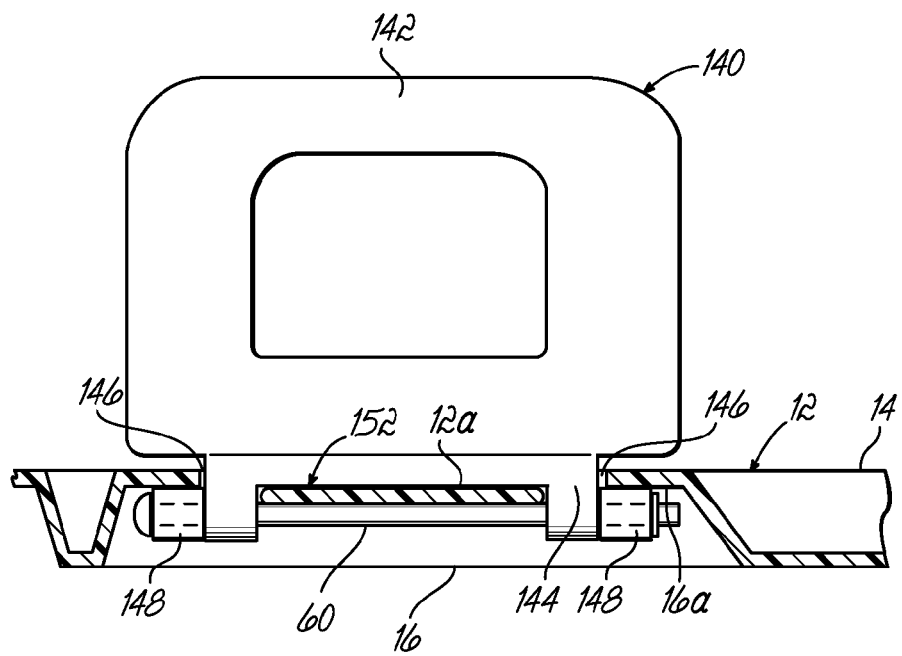
FIG. 19 is a side cross-sectional view of the embodiment in FIG. 18.

In an alternative embodiment of the invention, as illustrated in FIGS. 18 and 19, a specific index structure with discrete index positions, is not utilized to hold the paddle in position when it is moved to the support position. Rather, a friction fit between elements of the paddle and the backboard provides the fixation of the paddle in a specific position. More specifically, the spanning portion and paddle body rest against respective back side and front side surfaces to secure the paddle in place in the support position. Referring to FIG. 18, paddle 140 has a paddle body 142 that moves between a support position and a storage position, as discussed above. One or more leg portions 144 depend from the paddle body and extend through respective slots 146 formed in the backboard. A spanning portion 60, such as a dowel, spans from the leg portion or spans between and is secured by the leg portions 144. In one embodiment, the spanning portion and paddle may be configured to pinch the backboard there between when the paddle is moved to the support position. That is, no index structure is utilized and the friction provided at the front and back sides of the backboard will hold the paddle in place. Alternatively, cam structures might be used as illustrated in FIGS. 18, 19. Positioned on the spanning portion 60 are one or more cams 148, which are configured to engage a back side 16 or a portion of the backboard to lock the paddle when it is in the support position, as illustrated in FIGS. 18 and 19. In the embodiment illustrated in the Figures, two cams 148 are utilized, one associated with each of the leg portions 144 extending through the backboard. Referring to FIG. 18, when the paddle 142 is moved to the support position, the cam 148 includes a flat surface 150, which engages a back side surface 16a of a portion of the backboard. Simultaneously, a portion of the paddle 152 engages a front side section 12a of the backboard. The cam 148 rolls about its pivot axis, which is generally co-axial with the dowel 60 to pinch itself and the paddle against respective surfaces of the backboard. For example, the surface 150 of cam 148 is directed against surface 16a, while the paddle is directed against surface 12a. The pinching provides a frictional engagement or interference with the backboard, such that the paddle is locked into the support position, as desired for supporting the head and neck of a patient. One advantage of the embodiment illustrated in FIGS. 18 and 19 is that discrete index positions are not utilized. Rather, the paddles may be adjusted to a seemingly infinite number of different head widths along the continuous respective backboard surfaces 12a, 16a. The cam 148 provides a wedging or pinching action in the support position; however, when the paddle is moved from the support position toward the storage position, the cam is free to pivot such that the flat surface 150 disengages from surface 16a to allow lateral movement of the paddle to a desired position.

FIG. 20 illustrates another embodiment of the present invention wherein the index structure 70 is utilized on the back side 16 of the board. Referring to FIG. 20, similar reference numerals are utilized to note similar elements. The index structure 70a utilizes grooves 72a at various index points along the index structure. The spanning portion 60, such as a dowel, and the grooves 72a are configured such that the dowel can engage the grooves when the dowel is moved to the support position, as illustrated in FIG. 20. A bottom surface of the paddle 74a engages surface 16 of the backboard, and the paddle is thereby locked into position.

FIGS. 21-24 illustrate another embodiment of the invention, and particularly another paddle structure and backboard device utilized to form the immobilization device of the invention. Specifically, the paddle 200 in FIGS. 21-24 has various characteristics that provide additional advantages and benefits. Paddle 200 utilizes a frictional engagement for fixation, somewhat similar to the paddle of FIGS. 18 and 19.

Paddle 200 may be made of a suitable material, such as a plastic material, and similar to other paddles disclosed includes generally head-engaging portion 202, which extends above the backboard 204, and one or more leg portions 206, which extend through respective slots 207 in the backboard 204 and extend below the backboard as illustrated in FIGS. 21-24. Backboard 204, similar to other backboard embodiments described herein, has a front side 208 and a back side 209. Generally, a patient is placed on the front side with his head positioned between the opposing paddles (see FIG. 2). In accordance with one aspect of the present invention, paddle 200 includes opposing friction surfaces that capture a section of the backboard there between for securing the paddles in a lateral support position on the backboard when they are folded up from the storage position, such as to support the patient's head.

Figure 21:
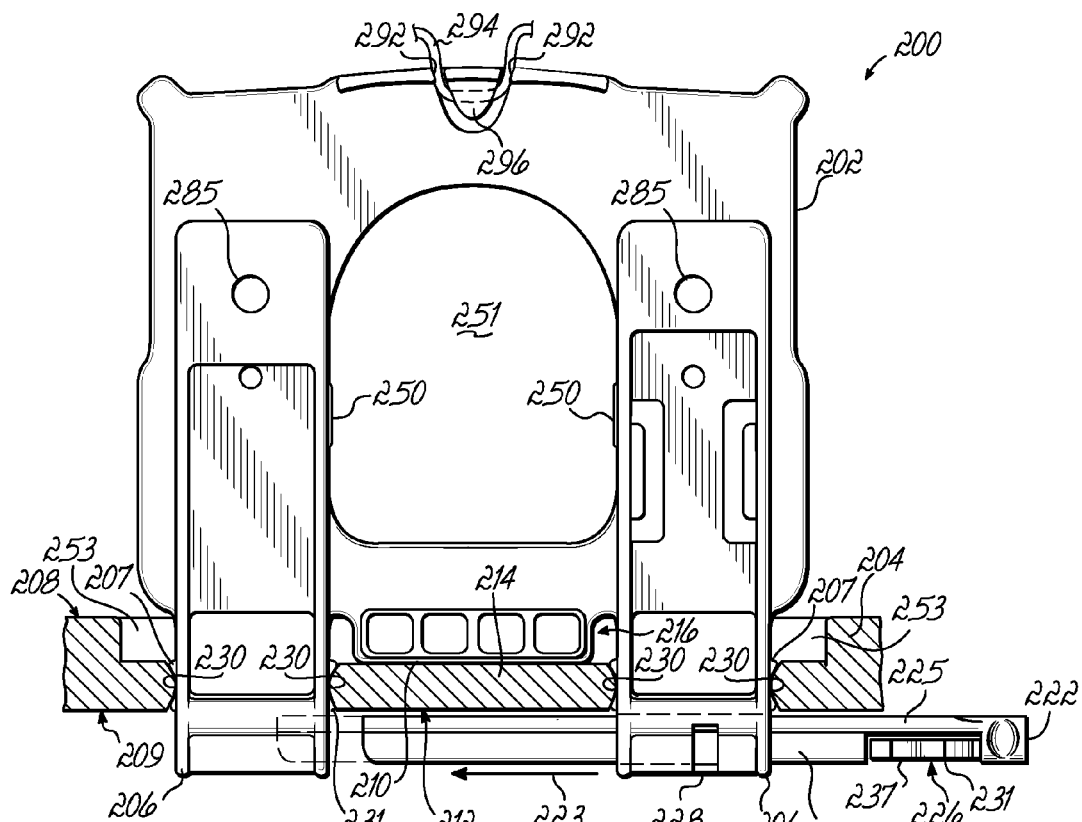
FIG. 21 is a side view of the paddle of the invention in the support position.
Figure 24:
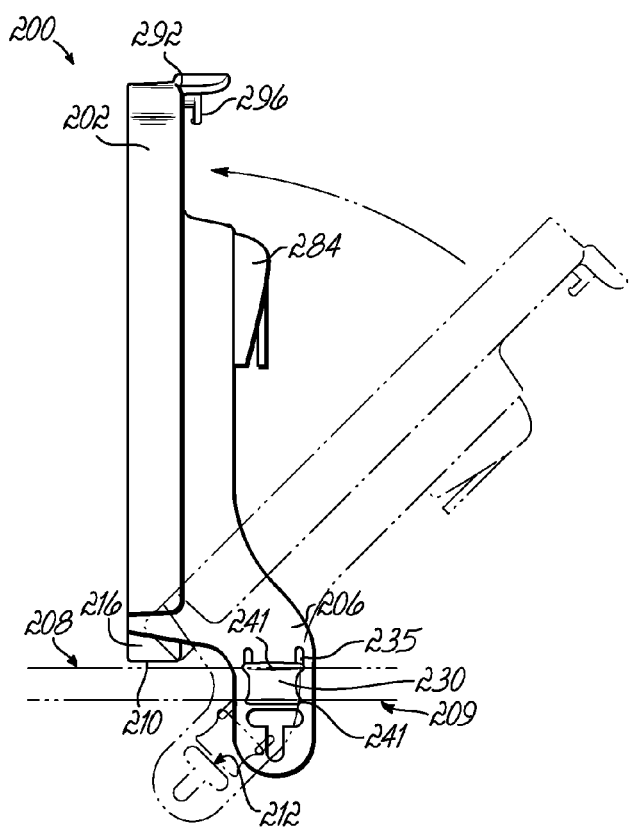
FIG. 24 is an end view of a section of the backboard illustrating the paddle moving between the storage position and the support position.

Specifically, referring to FIG. 21, the paddle includes a first friction surface 210 and a second opposing friction surface 212, which basically oppose each other on opposite sides of the backboard 204. In FIG. 21, a section 214 of the backboard is defined by slots 207 and is sandwiched between the opposing friction surfaces 210, 212. In the embodiment illustrated in FIG. 21, the head-engaging portion 202 includes a downwardly extending rib 216 along its bottom edge, which defines the first friction surface 210. The rib 216 and its friction surface 210 engage the top side 208 of the backboard section 214 (see FIG. 24). That is, when a paddle 200 is moved to the support position, as illustrated in FIGS. 21 and 24, the rib 216 is positioned such that friction surface 210 rests against or is forced against surface 208 of the backboard section 214. The board and paddle, including rib 216, may be plastic or rubber. Alternatively, one of surface 208 or 210 might include a rubberized or friction-enhancing portion, although it is not necessary as the material of the parts may provide sufficient friction. That is, the friction may just be provided by contacting surfaces. For example, a rubber or other material boot 217 might be used on rib 216 to create and enhance friction (see FIG. 22). Also, a strip or section of rubber or other friction material might be used on the backboard to underlie rib 216 and create or enhance friction. One or both such friction-enhancing elements might be used.

Figure 23:
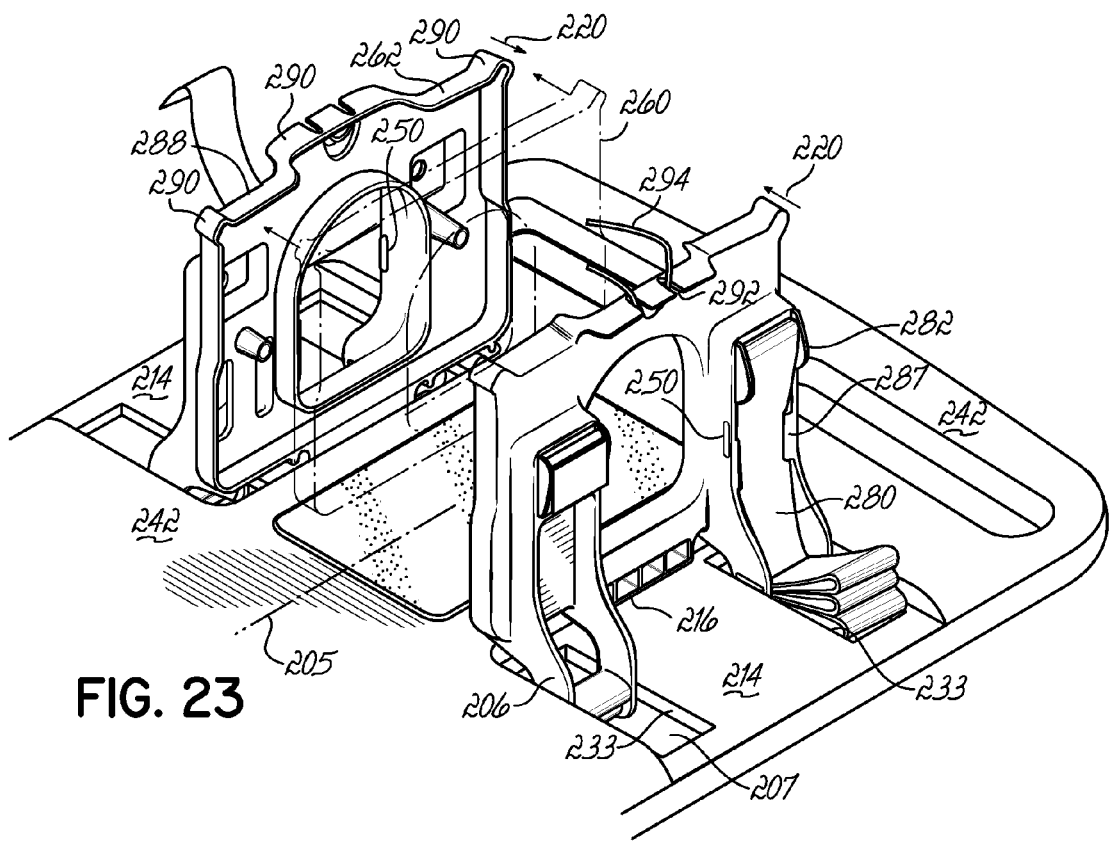
FIG. 23 is a perspective view of a portion of the backboard showing the paddles in the support position.

Simultaneously, second friction surface 212 is also forced against the back side 209, as illustrated in FIG. 24. The first and second friction surfaces 210, 212 engage the backboard together, and thereby frictionally fix the lateral position of the paddle on the backboard as shown in FIG. 23. Specifically, when the paddles are in their support position with the patient's head captured there between, they will be strapped together or otherwise secured together against the patient's head and would thereby be forced in the direction of reference arrows 220, as illustrated in FIG. 23. Referring again to FIG. 24, this forces both friction surfaces 210 and 212 against respective surfaces of the backboard, and thereby provides friction that resists lateral movement of the paddles to fix the lateral position of the paddles and generally prevent them from sliding laterally on the backboard and away from the desired positions at the patient's head.

Referring to FIG. 24, if the paddle is moved between the storage position and the support position, the leg portion 206 moves in a generally arcuate position as noted above to bring the friction surface 210 down to surface 208 and the friction surface 212 up to surface 209 for frictional engagement. As such, paddle 200 does not utilize, in index structures, in the form of grooves, slots, or other structures for securing its lateral position. This feature enhances the maintenance of the device. Specifically, the surfaces 208, 209 of the backboard section 214 are smooth and allow for easier cleaning and maintenance. There is less structure to capture dirt, germs, and bodily fluids. Paddle 200 can be formed of any suitable material, such as a light weight plastic and may be formed as a single piece, as illustrated in the drawings, or might be in multiple pieces, such as a separate head-engaging portion 202 and separate leg portion 206, which are then bolted or otherwise secured together.

Figure 22:
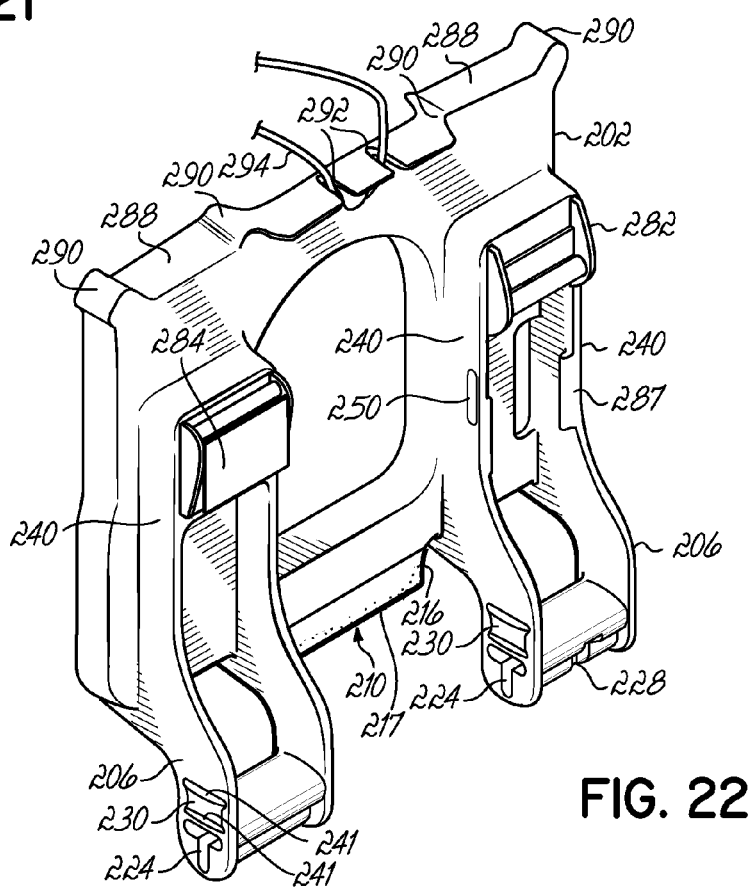
FIG. 22 is a perspective view of the paddle of the invention.
Figure 28:
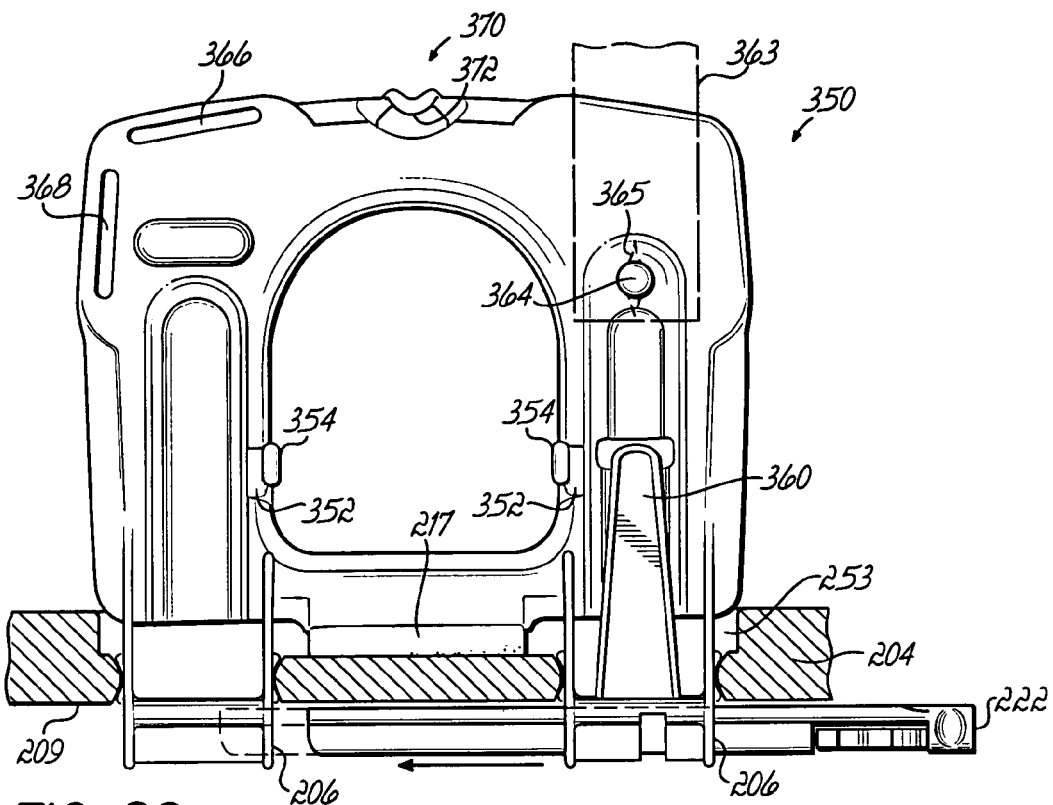
FIG. 28 is a front view of an embodiment of a paddle in the support position.

In another aspect of the present invention, the paddles 200 are removable from the backboard. A portion of the paddle extends through a slot in the backboard as shown in FIGS. 23 and 28. A structure then is configured to cooperate with the paddle portion and to secure the paddle with the backboard. For example, in the embodiments illustrated in FIGS. 21-24, a structure includes a removable pin or pin structure 222, which slides into an appropriately formed aperture 224 in the leg portions 206 of the paddle. The pin 222 cooperates with aperture 224 in the leg portion 206 that extends through slot 207. Referring to FIG. 21, the pin structure 222 may be slidably inserted into the leg portions 206 in the direction of arrow 223. The pin structure includes a snap structure 226, which engages the aperture 224 for locking the pin structure in place with the paddle to secure the paddle with the backboard. For example, to secure the paddle 200 with the backboard 204, the various leg portions 206 are extended through slots 207 and are configured to extend laterally with respect to the center longitudinal access 205 of the backboard, as illustrated in FIG. 23. Once the leg portions are completely through the slots 207, the pin structures 222 may be slid through the apertures 224 to extend through both leg portions 206, as illustrated in FIG. 21 and span below section 214. When the pin structure 222 is all of the way through the leg portions, the snap structure 226 engages the apertures, and specifically engages a cutout section 228 of one of the leg portions 206 (FIG. 22). As illustrated in FIG. 21, one embodiment of the pin structure has a snap structure that includes a flexible arm 237 extending there from, and having a head 231 to snap into position in the cut-out section 228 and, thereby, hold the pin structure in place to secure the paddle to the backboard. The paddle is then removed by removing the pin structure 222. To that end, the flexible arm 237 may be bent to disengage the head 231 from the cutout 228 and thereby slide the pin structure 222 in the opposite direction from arrow 223 and remove it from the apertures 224. With no structure spanning the board section 214, the paddle may then be pulled out of the backboard. This feature of the invention allows the paddle to be secured with the backboard for storage, but then readily removed for cleaning and for replacement.

In one embodiment of the invention, the pin structure 222 has a vertical section 222a and a horizontal section or cross piece 225. The sections 222a and 225 form a T-shaped cross-section, which corresponds to a T-shaped cross-section of the aperture 224. The relatively wide cross piece 225 defines a second friction surface 212. The widened cross piece provides an increased surface area for the friction surface 212 and, thus, enhances the overall frictional fixation of the paddle in its proper place in the support position.

Figure 31:
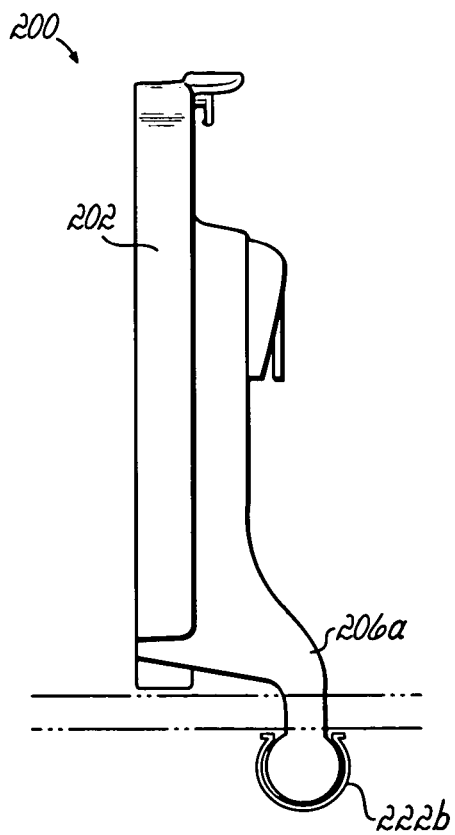
FIG. 31 is a side view of an alternative embodiment of a paddle.
Figure 32:
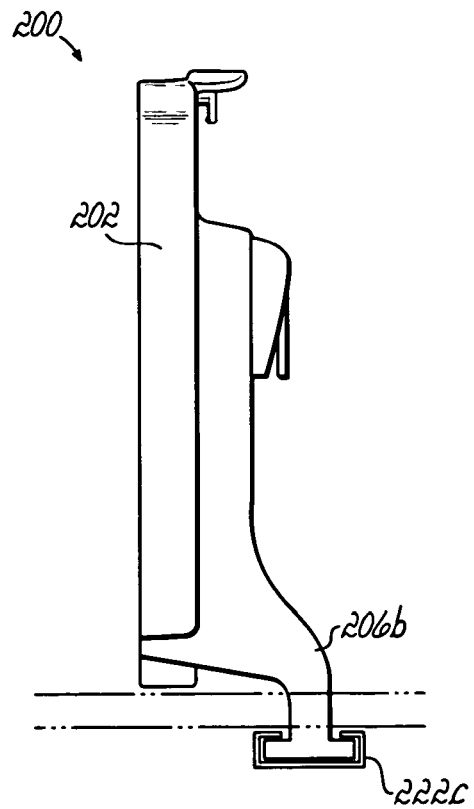
FIG. 32 is a side view of an alternative embodiment of a paddle.

In another embodiment of the invention, the structure configured to cooperate with the paddle portion and to secure the paddle with the backboard might be a shaped element that operably engages the paddle portion for securement. Referring to FIGS. 31 and 32, the leg portion 206a extending through the slot in the backboard might be shaped with a specific shape to match or cooperate with a shaped element 222b. The securing structure includes the shaped element 222b that operably engages the paddle portion 206a to secure the paddle. Although FIG. 31 shows a paddle portion 206a with a rounded cross-section and a shaped element 222b with a C-shaped cross-section, other shapes may be used as well. For example, FIG. 32 illustrates a paddle portion 206b with a rectangular cross-section and a shaped element 222c with a rectangular C-shape. The elements 222b, 222c clip or snap on to the leg portions to secure the paddle.

In accordance with another aspect of the present invention, paddle 200 utilizes a snap structure, or rather a plurality of snap structures 230, for maintaining the paddle in an upright or support position when it has not yet been secured around the head of the patient. The snap structure 230 are resilient and will give way when the paddle is folded up to a support position, as illustrated in FIG. 21.

The slots 207 formed in the backboard to receive the leg portion of the paddle have sidewalls 233. The sidewalls 223 are dimensioned to be engaged by the snap structures and to fit between ridges 241 of each snap structure 230. FIG. 24 illustrates a paddle in the support position, wherein the sidewalls 233 of the slots snap into engagement with the snap structure 230 to hold the paddle in the support position. As illustrated in FIGS. 21 and 22, the snap structures 230 are on either side of the leg portions 206 of the paddle, and thus engage the backboard proximate the slots and specifically at all of the sidewalls 233 of the slots 207. Alternatively, snap structures might be utilize with respect to only one leg portion 206, or could be only utilized on one side of the leg portion. For a more secure or snug engagement, the sidewalls 233 of the slots might be configured to closely engage each snap structure 230. For example, as shown in FIG. 21, the sidewalls 233 might be rounded to engage a rounded or concave surface of the snap structure. Alternatively, the slot sidewalls might be concave to receive a convex or outwardly rounded surface of the snap structure.

The snap structure 230, as illustrated in the disclosed embodiment, cantilevers with respect to the leg portions 206, generally as a tongue formed by parallel slots 235 illustrated in FIG. 24. Alternatively, the snap structure may be any other suitable, resilient snap structure, which will allow the paddle to be snapped into engagement against the sidewalls of the slots, or vice versa. FIG. 21 illustrates how four snap structures 230 secure the paddle in the support position. The paddle 200 may be slid laterally in the support position as illustrated in FIG. 21 with the snap structures engaged. However, the paddle might be more readily slid into position by folding the paddle somewhere between the storage position and the support position as illustrated in FIG. 24 to disengage the snap structures from the sidewalls 233.

As illustrated in FIG. 22, the leg portions 206 extend away from the head-engaging portion 202 of the paddle, both downwardly and to one side. More specifically, the leg portions 206 include sidewalls 240, which extend away from the head-engaging portion of the paddle and form strap-containing areas there between, as discussed further herein below. When the paddle is moved to the storage position, it generally would lie flush against the backboard, and generally flush with the front side 208 of the backboard. For a flush engagement, the backboard portion 214 and slots 207 are recessed, as illustrated in FIG. 23, below the main front side surface 242 of the backboard. Furthermore, the leg portions 206 are dimensioned to be received into the slots for the paddle to lie flush in the storage position.

In accordance with another aspect of the present invention, the paddles utilize small securement ribs 250 on either side of the leg portions and positioned generally proximate the walls of the ear opening 251 in the paddle 200 (See FIGS. 21-22). A recess 253 is formed in the backboard for each paddle. When the paddle is folded down to the storage position, the paddles fit into the recesses 253 and lie generally flat against the backboard. The ribs 250 are compressed as the leg portions 206 pass through the slots 207. The ribs 250 snap out on the other side of the slots and engage the backboard proximate the recess and specifically proximate the back side 209 to secure the paddles in the storage position and prevent them from inadvertently flapping around or falling out of the storage position to the support position when the backboard is stored and/or moved, such as to the site of the patient. More specifically, as illustrated in FIG. 21, the ribs 250 are opposing and, thus, snap around the walls 233 of the slots adjacent to the backboard back side 209. As such, the paddles are snapped around the backboard portion 214 in the storage position and are held therein by the opposing ribs 250. The ribs can move in/out generally due to the flexibility of the ribs and/or the sidewalls 240. In one embodiment, the ribs are simply formed as a portion of the paddle. Alternatively, they might be separate pieces attached to the paddle. To move the paddles to the support position, the paddles are simply grasped and rotated upwardly. The ribs 250 are disengaged and the snap structure 230 is subsequently engaged when the paddle is pulled completely upward to the support position (FIG. 24).

In accordance with another aspect of the present invention, the paddles 200 utilize a pliable element, such as a pliable pad for providing comfort to the patient's head. The pliable element pad 260 (see FIG. 23) is made of a suitable pliable material, such as a foam or other pliable plastic material. A pad is illustrated as one embodiment, but another embodiment might also be utilized. The pliable element is removably mounted to the head-engaging portion 202 of the paddle 200. For example, the pliable pad is generally in the shape of the head-engaging portion of 202 of the paddle 200. The head-engaging portion 202 has sidewalls there around 262, which form a cup structure. The pad 260 is removably mounted in the cup structure formed by the sidewalls 262 of the paddle. Preferably, the pliable pad's dimension is slightly largely than the cup structure of the head-engaging portion, so that the pad may be frictionally mounted in the cup structure and held therein, generally without fasteners. In that way, the pliable pad 260 may be removed for cleaning and/or replacement. Removing the pad will also allow the paddle to be more readily cleaned. Although with a friction fit, no fasteners are necessary, fasteners or adhesives might be utilized to hold the pad 260 in position with the paddle. For example, one or more posts 261 might be used in the cup structure to hold pad 260 in position (See FIGS. 29 and 30) by friction. Therefore, the paddles may be readily removed from the backboard and the pads may be readily removed from the paddles, all for maintenance and cleaning purposes.

Figure 25:
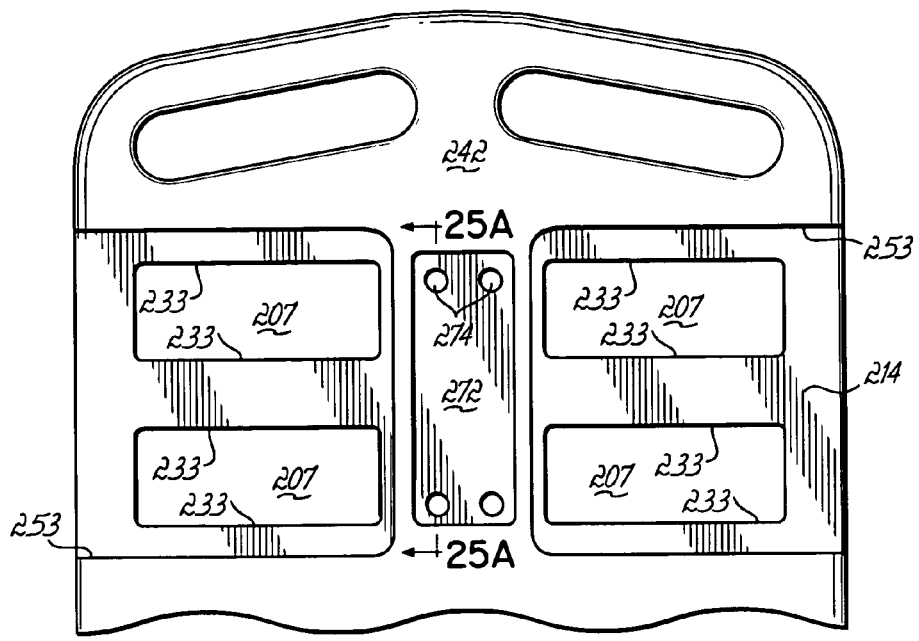
FIG. 25 is a top view of a section of a backboard in accordance with the present invention.
Figure 25A:
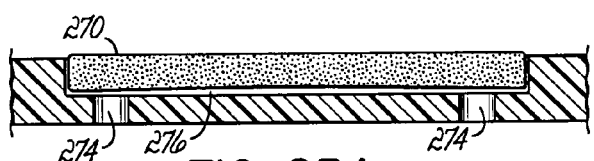
FIG. 25A is a partial cross-sectional view along lines 25A-25A of FIG. 25.

In accordance with another aspect of the present invention, a pliable pad 270 is also positioned between the paddles along the front side of the backboard, as seen in FIGS. 23 and 25A. The pad 270 is mounted in a recess 272 and is configured to frictionally fit inside the recess. That is, the pliable pad 270 would generally be sized slightly larger in dimension than the size of the recess 272. Alternatively, fasteners or adhesives might be utilized to hold the pliable pad in the recess 272. Preferably, however, the pliable pad frictionally engages the recess 272 to be readily removable, such as for cleaning or replacement. As shown in FIG. 25, the recess 272 creates an area behind the patient's head wherein bodily fluid from an immobilized patient might collect. In accordance with another aspect of the present invention, one or more drain holes 274 are formed in the recess 272 and the drain holes extend through the floor of the recess, and generally through the thickness of the backboard for draining fluid out of the recess 272. In that way, excess fluid is not trapped by the backboard. Furthermore, when the backboard is cleaned, water and other cleaning fluid can be drained out of the holes, carrying away any undesirable bodily fluids or other fluids.

Figure 25B:
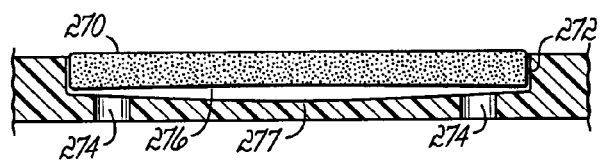
FIG. 25B is a view similar to FIG. 25A, for an alternative embodiment of the invention.

In accordance with another aspect of the present invention, the bottom surface 276 of the pliable pad 270 is contoured, as illustrated in FIG. 25A to extend partially above the recessed floor and above the drain holes 274. Alternatively, the floor 277 of the recess 272 might also be contoured as shown in FIG. 25B. In that way, the fluid can more readily drain through recess 272 and through the drain holes 274. The drain holes are not inadvertently plugged by the bottom surface of the pad 270.

Figure 25C:
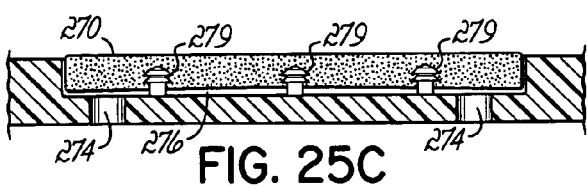
FIG. 25C is a view similar to FIG. 25A, for an alternative embodiment of the invention.

As illustrated in FIG. 25A, the pliable pad may be dimensioned to be generally flush with the top surface or front side of the backboard or may be elevated above the front side of the backboard in order to elevate the head to maintain cervical spine alignment when the pad is in position in the recess 272. Alternatively, the pad might be slightly below a flush level. As noted, the pliable pad may be friction fit inside of the recess, or might be secured with Velcro or other fastening means. For example, as illustrated in FIG. 25C, one or more posts 279 configured to extend into and grip the pad 270, may be used to secure the pad. Posts 279 might be integral with the backboard or fastened thereto in the recess. The pad may have one or more slits therein to receive the posts.

In accordance with another aspect of the present invention, the paddles are secured about the patient's head and secured in the support position utilizing integral straps that are coupled to and remain with the paddles. Specifically, as illustrated in FIG. 23, the securement straps 280 have a secured end and a free end. The secured end of the strap is secured to the paddle with an anchor structure 282, as shown in FIGS. 22 and 23. The anchor structure 282 is rotatable for securing the end of the strap in a rotatable fashion to the paddle. In one embodiment, the rotatable anchor structure 282 rotates between the 9 and 12 o'clock positions. This allows the strap to be properly positioned, such as across the forehead or chin of the patient. On the opposing paddle opposite the anchor structure is a buckle structure 284 for securing the free end of the strap, such as in a cam buckle arrangement. The buckle structure 284 is also rotatable and may rotate between the 9 and 12 o'clock positions, in one embodiment. Of course, other wider ranges of rotation may be used in the anchor structure and the buckle structure might rotate 360 degrees. The anchor structure and the buckle structure are securely coupled with the paddle, such as through appropriate openings 285 therein (see FIG. 21). In the embodiment illustrated in the present invention, each paddle includes one anchor structure and one buckle structure. Alternatively, one paddle might include both anchor structures and the other paddle might include both buckle structures. In any case, the strap remains with the paddle and is readily available for use when a patient is placed on the backboard. As illustrated in FIG. 23, when the strap is not being utilized, it may be folded up and pushed into an area between the opposing walls 240 of the leg structure. The folded strap is illustrated in FIG. 23. Extending into the area of the leg portion defined by the walls 240, are lips 287 under which the folded strap is captured until it is pulled out for usage. In that way, the strap is contained neatly on the paddle and will lie contained between the paddle and the backboard when the paddle is in the storage position. Folding the paddle up to a forward position will expose the strap, which may then be pulled out from behind the lips 287 and stretched across the head of the patient to be secured to the opposing paddle. FIG. 2 illustrates securement of the head between the paddles in one embodiment. In the embodiment illustrated in FIGS. 21-24, the strap goes over the top of the paddle and is generally dimensioned to fit between channels 288 formed by opposing ridges 290 along the top edge of the paddle. The channels 288 keep the straps aligned properly and prevent them from shifting around on the paddle.

In accordance with another aspect of the present invention, the head-engaging portion of a head engaging structure, like a paddle, may include an accessory mount that is configured for capturing an accessory used by the patient on the backboard to hold the accessory proximate the head of the patient. For example, an oxygen cannula might be attached to an appropriate oxygen supply for directing oxygen into the mouth or nose of a patient. Alternatively, an oxygen mask might be positioned over the patient's mouth. Generally, such a cannula will extend between the paddles and across the face and head of the patient. As such, to secure such accessories the prior art required that the devices or portions thereof be secured or held down, such as with tape or some other structure. In accordance with one aspect of the present invention, the accessory mount is generally integral or coupled with the head-engaging structure and, thus, is always available when the paddle is in use. To that end, in one embodiment of the invention, one or more slots 292 are utilized for securing the cannula 294 or other tube for holding the tube in place with respect to the paddles and the head of the patient. Furthermore, the accessory mount may include a clip structure 296, which further grabs a portion of the cannula 294 to keep it in place. In that way, the slots 292 and clip structure 296 cooperate to secure the accessory. An alternative accessory might include an oxygen mask that has side straps, which can be stretched over the clip structure 296 between the slots 292 to hold the mask across the paddles and over the mouth of the patient whose head is secured there between.

Figure 33:
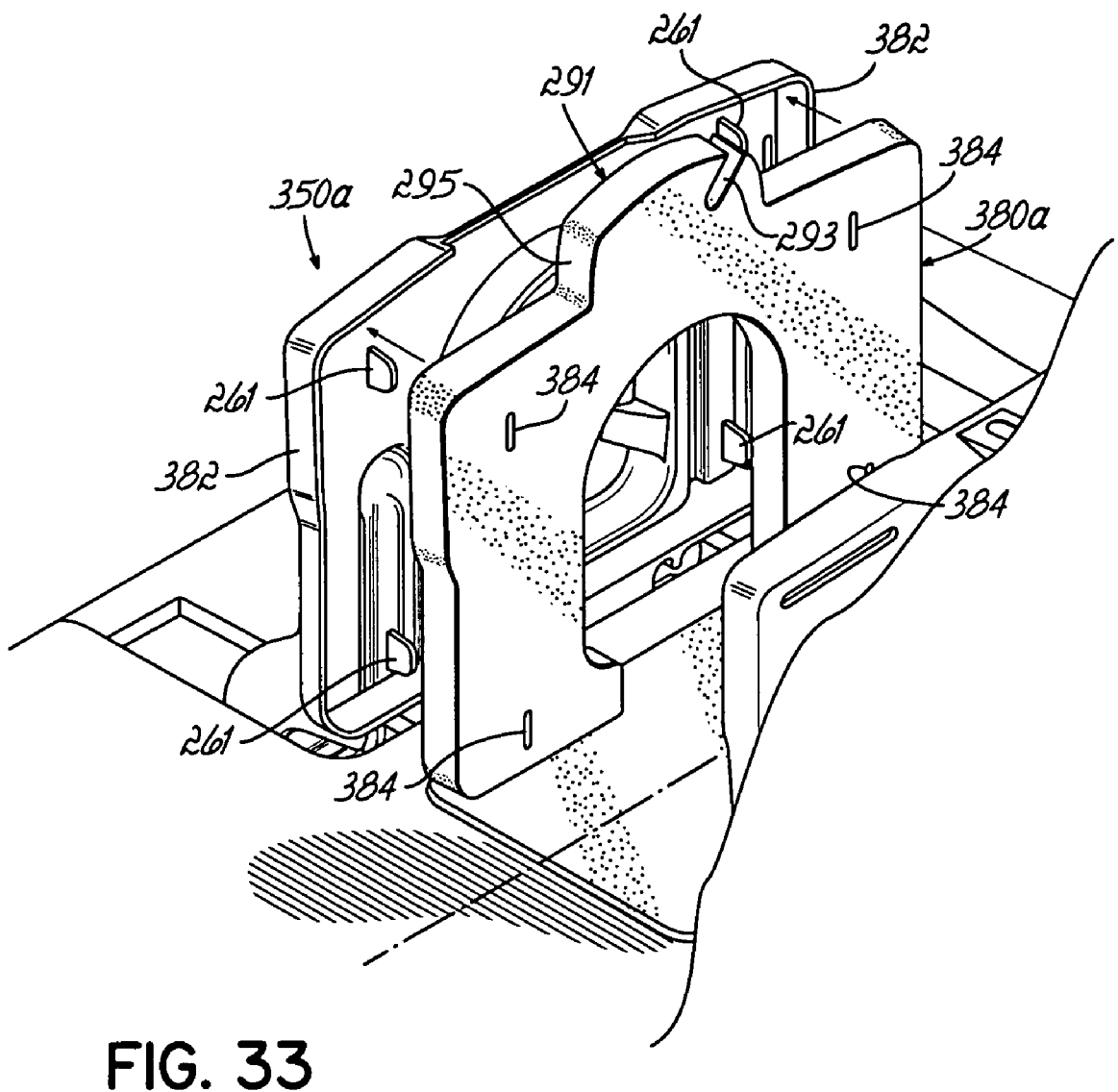
FIG. 33 is a perspective view of a paddle shown engaging a pad.

In an alternative embodiment, another portion of the head-engaging structure 200, 350 may include an accessory mount positioned thereon. For example, referring to FIG. 33, an accessory mount 291 is shown positioned on the pliable element or pad 380a. Specifically, accessory mount 291 is formed in pad 380a and may include a slit 293 formed in a lobe 295 that extends from pad 380a. A cannula or other tube glides into the slit 293 for securement. Therefore, the accessory mount may be positioned on various portions or components of the head-engaging structure.

Figure 26:
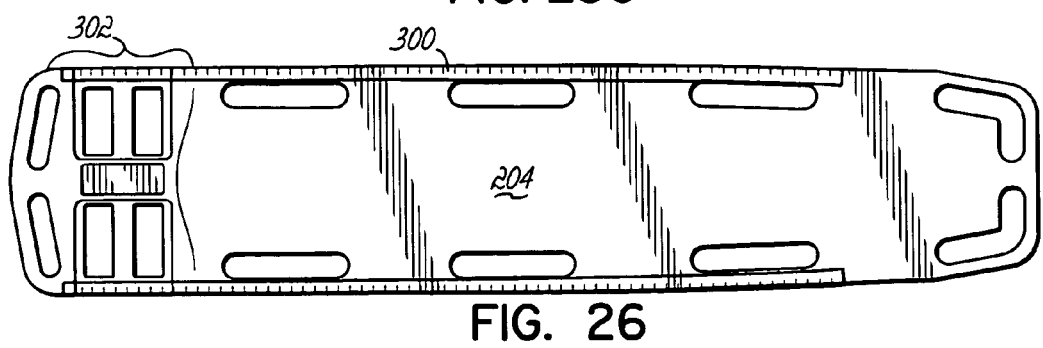
FIG. 26 is a top view of a backboard embodiment of the invention.

In another embodiment of the invention, as illustrated in FIG. 26, a backboard structure 204 includes ruler indicia 300 extending along the length of the backboard. The ruler indicia 300 might extend along the entire length of the backboard or along a portion of the length of the backboard. The ruler indicia includes a section 302 positioned proximate the paddles for use in positioning the patient's body and head with respect to the paddles. The ruler indicia 300 is preferably x-ray opaque, such that when x-rays are taken with the patient's head on the backboard, the ruler indicia can provide a reference for the patient's head and spine on the x-ray. For example, different hash lines might be formed as raised ribs, with the different heights of the raised ribs providing the x-ray opaqueness. Alternatively, low metallic paint might be used to form or enhance the ruler indicia 300 for x-ray purposes.

Figure 27A:
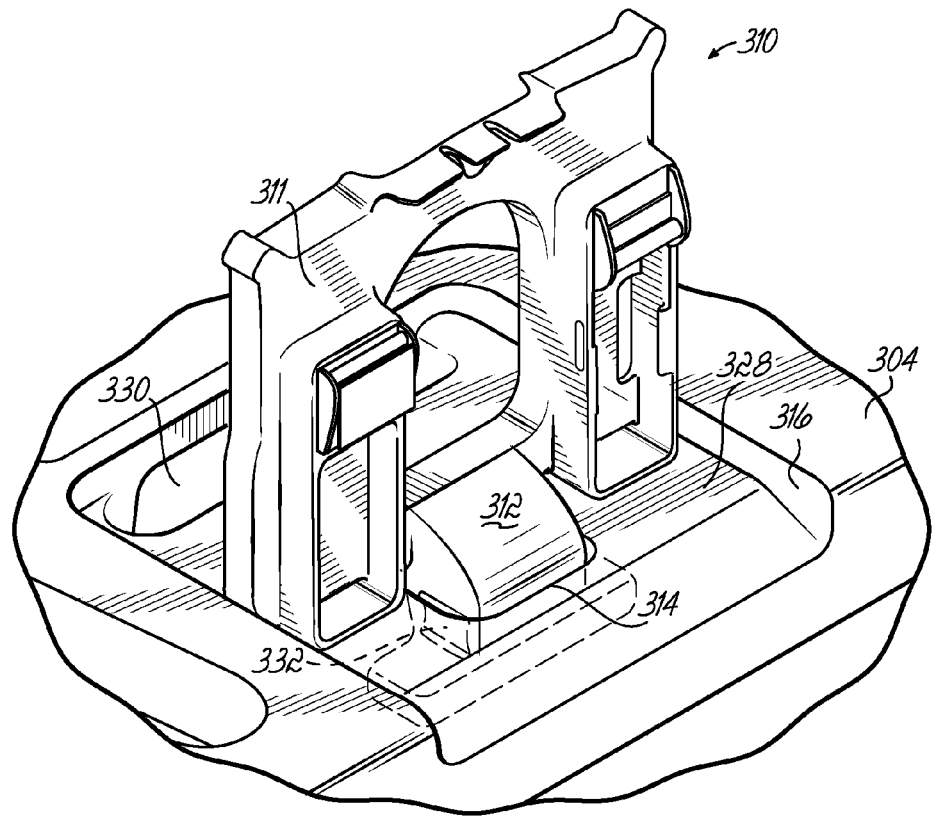
FIG. 27A is a partial perspective view of an alternative embodiment of a paddle of the present invention.
Figure 27B:
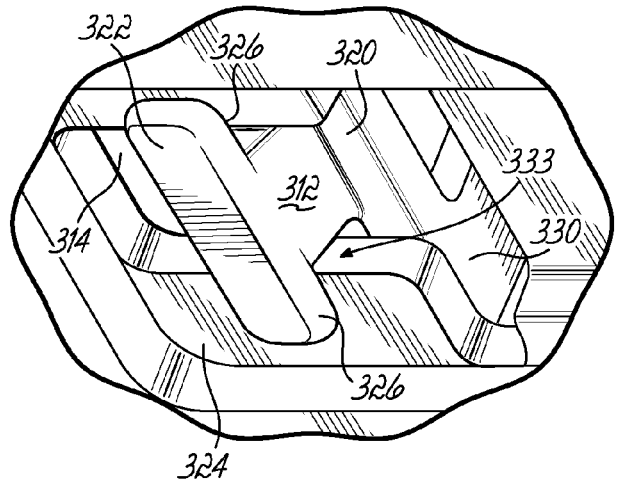
FIG. 27B is a partial bottom perspective view of the paddle of FIG. 27A.
Figure 27C:
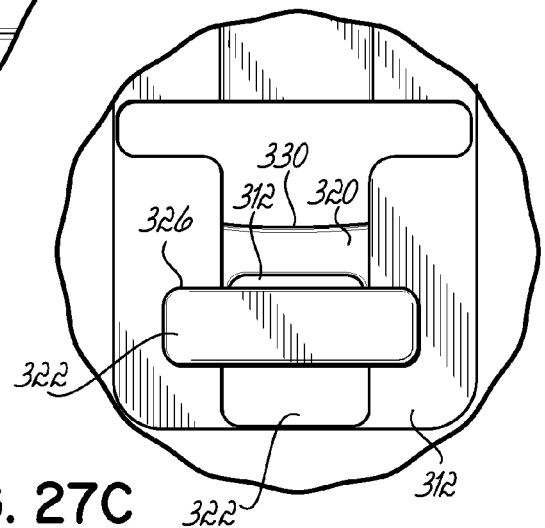
FIG. 27C is another perspective view of the paddles and backboard of FIG. 27A.

FIGS. 27A-27C illustrate an alternative embodiment of a paddle in accordance with one aspect of the present invention. Paddle 310, as illustrated in FIG. 27A, is similar in many ways to the paddles illustrated in FIGS. 21-24. However, it uses a single leg portion and does not utilize a removable pin structure for being removed from the backboard. Alternatively, paddle 310 includes a leg portion 312, which fits into and through a single slot 314 formed in the backboard. Paddle 310 is coupled to travel within a recess 316 in the backboard 304, and is configured to lie generally flat against the backboard in the storage position. The paddle may then be rotated up to the support position as illustrated in FIG. 27A.

Referring to FIG. 27B, the first friction surface is formed by a bottom surface 320 of the paddle head-engaging portion. The leg portion 312 then extends downwardly and through slot 314, to extend below the slot and proximate the backside of the backboard. The leg portion 312 includes a spanning portion 322, which extends laterally out to either side of the leg portion 312 in the slot 314, as shown in FIG. 27B. In the embodiment illustrated in the invention, the head-engaging portion 311, leg portion 312, and the spanning portion 322 are integrally formed together. Alternatively, they might be separate pieces that are coupled together with appropriate fastening means. The spanning portion spans to either side of the leg portion and engages the back side 324 of the backboard 304 when the paddle is in the support position. In one embodiment, a recessed area might be formed proximate back side surface 324. The spanning portion 322 thereby provides a second friction surface 326 to engage the back side surface 324. Surface 320 of the paddle provides the first friction surface, which engages the front side surface 328 of the backboard. The cooperating first and second friction surfaces thereby will secure the paddle in its desired lateral position when the paddle is moved to the support position and secured on either side of the head of a patient. That is, rotating or pulling the paddle 310 toward the head of the patient will drive surface 320 down against surface 328 and drive surface 326 upwardly against surface 324.

Like the paddle of FIGS. 21-24, the paddle illustrated in FIGS. 27A-27C is also removable from the backboard, although it is meant to be integrally stored with the backboard in a storage position. Rather than removing a removable pin structure, the slot 314 formed in the board 304 includes a cross slot 330 through which the spanning portion 322 may pass when the paddle is moved generally to the end of the slot 314 closest to the center longitudinal access of the board, as illustrated in FIG. 27C. In that furthest most center position, the paddle 310 can then be rotated slightly backwardly toward the storage position wherein the spanning portion 322 can readily be manipulated through the cross-slot 330 to remove the paddle from the backboard. Similarly, reversing the procedure will install the paddle back onto the backboard so that it may be slid thereon. The paddles may be removed for maintenance or cleaning.

Referring to FIG. 27A, similar to the paddle 200, paddle 310 also includes a snap structure 332 that may be utilized to engage the side surface of the slot 314 to thereby snap the paddle into the support position, as described above. The snap structure 332 may have a similar configuration to the snap structure 230 discussed above. Similarly, the edges 333 of the slots might be contoured, such as by being rounded to more securely engage a rounded or other contoured surface of the snap structure 332.

Figure 29:
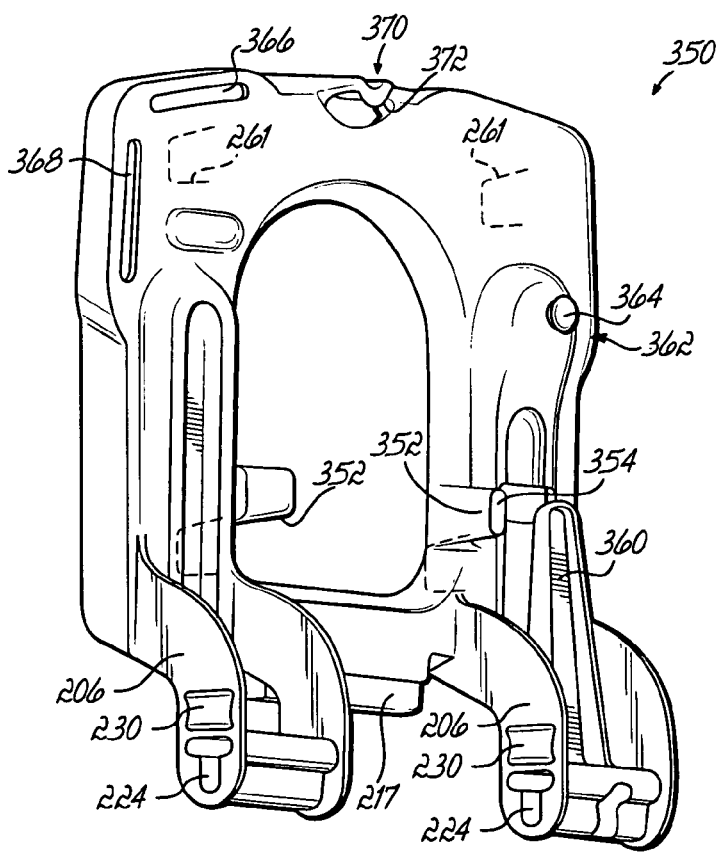
FIG. 29 is a perspective view of the paddle of FIG. 28.
Figure 30:
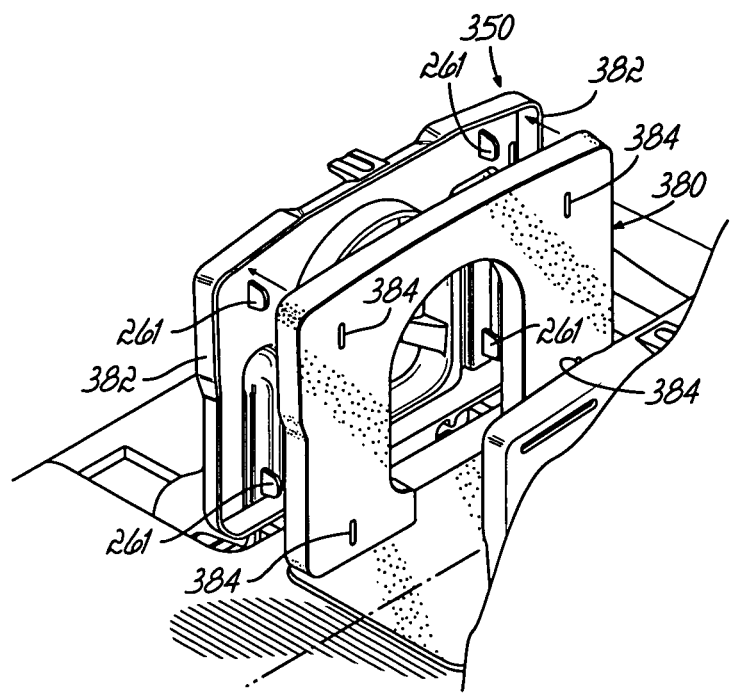
FIG. 30 is a perspective view of a paddle shown engaging a pad.

FIGS. 28, 29, and 30 illustrate further alternative embodiments of the invention. Specifically, these Figures illustrate alternative paddle designs and pad designs that may be utilized in accordance with the invention. The alternative paddle 350 is similar in many respects to paddle 200, illustrated in FIGS. 21-24. Therefore, like reference numerals are utilized. The paddle 350 may be similarly fixed to a backboard, as is paddle 200, shown in FIG. 21. Referring to FIG. 28, leg portions 206 extend into slots 207 on the board and are held therein by a pin structure 222.

Paddle 350 includes rearwardly extending wings or posts 352, which include thereon securement ribs 354, similar to securement ribs 250 in FIGS. 21, 22. When the paddle is folded down to the storage position, the paddles fit into the recesses 253 and lie generally flat against the backboard. The posts 352 are spread apart along with the ribs 354. As paddle 350 is moved to the storage position, the wings extend through the slots and the ribs 354 snap out on the other side of the slots and engage the backboard proximate the recesses and specifically proximate the back side 209 of the backboard to secure the paddles in the storage position.

When the paddles are in the support position, as illustrated in FIG. 28, the snap structures 230 are illustrated and operate as discussed above.

In accordance with the paddle embodiment 350, the leg portions 206 do not include the sidewalls 240, which form strap-containing areas therebetween, as illustrated in FIGS. 21 and 22. Rather, paddle 350 utilizes a flexible spring clip 360, which extends upwardly from the leg portions 206 when the paddle is in the support position. As illustrated in the Figures, the spring clip extends generally parallel to the body of the paddle 350. Spring clip 360 is spaced away from paddle 350 to form a strap-containing space therebetween. When the backboard is to be stored, the strap may be folded, as illustrated in FIG. 23, and the folded strap may be captured between the paddle 350 and the spring clip 360. In that way, the paddle 350 provides a positive securement of the folded and stored strap. As illustrated in FIGS. 28 and 29, a single spring finger 360 is utilized on each paddle for securing a single strap on each panel. Alternatively, both spring fingers might be utilized on the same paddle 350. Preferably, spring finger 360 is formed of a resilient metal or plastic for providing a positive capturing force against the strap.

For anchoring a secured end of a strap to the paddle 350, a post 362 is formed on the body of paddle 350 generally above the spring finger 360. The post 362 includes an enlarged head or nipple 364. A strap 363 to be utilized with the paddle 350 has a slot 365 at one end through which a portion of the post 362 and the head 364 extends (See FIG. 28). Preferably, the head 364 is wider than the slot 365 and, thus, provides securement of one end of the strap. When the paddles are in the support position, the other end of the strap may be pulled across to span between the paddles and be secured to the opposite paddle, such as with a buckle, Velcro or some other appropriate fastening mechanism. For example, the strap 363 may extend from one paddle to the opposing paddle and pass through the slots 366, 368. For cleaning or replacement, the slit strap may then be removed by pulling the strap such that the post and head pass back through the slot therein. A new strap may be replaced on the paddle 350 in the same way so that one end of the strap is secured.

The free end of the strap 363 passing to the opposite paddle is passed through one of a horizontal slot 366 or a vertical slot 368 before being secured. For example, the free end of strap 363 might fold back onto itself after passing through the slots and, therefore, might be secured, such as with Velcro. If the free end passes through the slots 366, 368 and the secured end is secured at the post 362 on the opposite paddle.

Paddle 350 also includes an accessory mount 370 for capturing an accessory used by the patient on the backboard. Referring to FIGS. 28 and 29, the accessory mount 370 might include a clip structure 372 that might be configured to grab a portion of a cannula or straps of an accessory, such as an oxygen mask, in order to hold such devices in place proximate the paddle 350 and proximate the head and neck of the person secured on the backboard. Alternatively, one or more post structures might be used for an accessory mount 370, such as to simulate the clip 372 or slots 292.

Paddle 350 is secured in the storage position and the support position, similar to the paddle 200 as illustrated in FIGS. 21-24, as discussed hereinabove.

FIG. 30 illustrates the paddle 350 and a pliable pad 380, which engages the paddle. As illustrated, pad 380 is configured to fit into the paddle and specifically into a cup structure formed by the sidewalls 382. The pad 380 is shaped approximately for engagement with the paddle and has a unique shape to allow clearance of the straps or other fastening means spanning between the paddles. For example, straps 363 fitting into slots 366, 368 do not interfere with the pad or are not hindered due to the unique shape of the pad. The pad 380 has slots 384 therein for receiving the posts 261 and frictionally engaging the posts to hold it into position as shown in FIG. 30. Other fastening means might be utilized as well to hold the pad in the paddle, such as Velcro or and adhesive.

While the present invention has been illustrated by a description of various embodiments and while these embodiments have been described in considerable detail, it is not the intention of the applicant to restrict or in any way limit the scope of the appended claims to such detail. For example, various features are shown for the different embodiments, but those features do not have to all be used on a single device. Different combinations of features and components might be used on various different embodiments of the immobilization device. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A patient immobilization device comprising:
a backboard having a front side and a back side;
at least one paddle mounted on the backboard and configured to rotate between a storage position where the paddle is generally down on the backboard and a support position where the paddle is up from the backboard, to support the head of a patient on the backboard;
a first friction surface of a paddle positioned proximate a front side surface of the backboard;
a second friction surface of a paddle positioned proximate a back side surface of the backboard;
the first and second friction surfaces effectively disengaging from the respective backboard surfaces when the paddle is rotated to a position between the storage and support positions so that the lateral position of the paddle may be adjusted on the backboard to adjust to a patient;
the first and second friction surfaces of the paddle engaging the respective backboard surfaces together when the paddle is rotated up to the support position to frictionally fix the lateral position of the paddle.

2. The device of claim 1 wherein the second friction surface is positioned laterally from the first friction surface.

3. The device of claim 1 further comprising a rib positioned on the paddle, the rib defining the first friction surface.

4. The device of claim 1 further comprising a pin structure coupled with the paddle proximate the back side of the backboard and defining a second friction surface.

5. The device of claim 4 further comprising a leg portion depending from a paddle and extending through a respective slot formed in the backboard between the front and back sides of the backboard, the pin structure engaging the leg portion and securing the paddle to the backboard.

6. The device of claim 4 wherein the pin structure has a cross piece forming the second friction surface.

7. The device of claim 1 wherein one of the first and second friction surfaces is laterally spaced from the other friction surface along the width of the backboard.

8. The device of claim 1 wherein the paddle storage position is generally against the board, the paddle including at least one securement structure for engaging the backboard in the storage position to lock the paddle in the storage position.

9. The device of claim 8 further comprising a post extending from the paddle, the securement structure positioned on the post.

10. The device of claim 9 wherein the post is flexible for flexing the structure against the backboard to lock the paddle in the storage position.

11. The device of claim 1 further comprising at least one slot formed in the backboard, a portion of the paddle extending through the slot, a structure on the paddle engaging the backboard proximate the slot when the paddle is in the support position to lock the paddle in the support position.

12. A patient immobilization device comprising:
- a backboard having a front side and a back side;
- at least one paddle slidably mounted on the backboard and configured to rotate between a storage position where the paddle is generally down on the backboard and a support position where the paddle is up from the backboard to support the head of a patient on the backboard;
- the paddle forming a first friction surface positioned proximate the front side of the backboard;
- a portion of the paddle extending through a slot in the backboard;
- a structure configured to cooperate with the paddle portion that extends through the slot to secure the paddle with the backboard;
- the structure forming a second friction surface positioned proximate the back side of the backboard;
- the first and second friction surfaces effectively disengaging from the respective backboard sides when the paddle is rotated to a position between the storage and support positions so that the lateral position of the paddle may be adjusted on the backboard to adjust to a patient;
- the first and second friction surfaces of the paddle engaging the respective backboard sides together when the paddle is rotated up to the support position to frictionally fix the lateral position of the paddle.

13. The device of claim 12 wherein the paddle portion includes an aperture, the structure including a pin that engages the aperture for securing the pin structure therein.

14. The device of claim 13 wherein the pin includes a snap structure with a flexible arm extending from the pin structure, the aperture including an opening for receiving a portion of the flexible arm for locking the pin structure in place.

15. The device of claim 12 wherein the structure includes a shaped element that snaps onto the paddle portion to secure the paddle with the backboard.

\* \* \* \* \*